(12) United States Patent
Baxter, III et al.

(10) Patent No.: US 7,766,209 B2
(45) Date of Patent: Aug. 3, 2010

(54) SURGICAL STAPLING INSTRUMENT WITH IMPROVED FIRING TRIGGER ARRANGEMENT

(75) Inventors: Chester O. Baxter, III, Loveland, OH (US); James Bedi, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 97 days.

(21) Appl. No.: 12/030,424

(22) Filed: Feb. 13, 2008

(65) Prior Publication Data
US 2009/0200355 A1    Aug. 13, 2009

(51) Int. Cl.
*A61B 17/068*    (2006.01)
(52) U.S. Cl. .................... 227/176.1; 227/19; 227/180.1
(58) Field of Classification Search ................... 227/19, 227/175.1, 176.1, 178.1, 180.1
See application file for complete search history.

(56) References Cited

U.S. PATENT DOCUMENTS

| | | | |
|---|---|---|---|
| 3,490,675 A | 1/1970 | Green et al. | |
| 3,499,591 A | 3/1970 | Green | |
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,819,100 A | 6/1974 | Noiles et al. | |
| 4,331,277 A | 5/1982 | Green | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |
| 4,429,695 A | 2/1984 | Green | |
| 4,475,679 A | 10/1984 | Fleury, Jr. | |
| 4,500,024 A | 2/1985 | DiGiovanni et al. | |
| 4,505,414 A | 3/1985 | Filipi | |
| 4,520,817 A * | 6/1985 | Green | 227/176.1 |
| 4,522,327 A | 6/1985 | Korthoff et al. | |
| 4,530,453 A | 7/1985 | Green | |

(Continued)

FOREIGN PATENT DOCUMENTS

CA    2458946 A1    3/2003

(Continued)

OTHER PUBLICATIONS

Partial European Search Report, Application No. 09250355.6, dated Jun. 2, 2009 (6 pages).

(Continued)

*Primary Examiner*—Scott A. Smith

(57) ABSTRACT

A surgical stapling instrument including an actuator knob which can be moved from one side of the stapling instrument to another side in order to reposition the actuator knob without having to reposition the stapling instrument within a surgical site. A stapling instrument can include a pusher bar, a housing having a first side and a second side, and an actuator knob rotatably mounted to the pusher bar wherein the actuator knob can be configured to be rotated between a first position in which the actuator knob can be moved along the first side of the housing and a second position where the actuator knob can be moved along a second side of the housing. Alternatively, a surgical stapling instrument can comprise one or more actuator knobs which can be operably engaged and disengaged with a pusher bar in order to selectively utilize the actuator knobs.

25 Claims, 19 Drawing Sheets

U.S. PATENT DOCUMENTS

| | | |
|---|---|---|
| 4,566,620 A | 1/1986 | Green et al. |
| 4,573,622 A | 3/1986 | Green et al. |
| 4,580,712 A | 4/1986 | Green |
| 4,610,383 A | 9/1986 | Rothfuss et al. |
| 4,629,107 A | 12/1986 | Fedotov et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,817,847 A | 4/1989 | Redtenbacher et al. |
| 4,821,939 A | 4/1989 | Green |
| 4,869,414 A | 9/1989 | Green et al. |
| 4,869,415 A | 9/1989 | Fox |
| 4,941,623 A | 7/1990 | Pruitt |
| 4,944,443 A | 7/1990 | Oddsen et al. |
| 5,065,929 A | 11/1991 | Schulze et al. |
| 5,083,695 A | 1/1992 | Foslien et al. |
| 5,129,570 A | 7/1992 | Schulze et al. |
| 5,137,198 A | 8/1992 | Nobis et al. |
| 5,221,036 A | 6/1993 | Takase |
| 5,263,629 A | 11/1993 | Trumbull et al. |
| 5,395,034 A * | 3/1995 | Allen et al. ............... 227/178.1 |
| 5,417,361 A | 5/1995 | Williamson, IV |
| 5,480,089 A | 1/1996 | Blewett |
| 5,482,197 A | 1/1996 | Green et al. |
| 5,485,947 A | 1/1996 | Olson et al. |
| 5,485,952 A | 1/1996 | Fontayne |
| 5,487,499 A | 1/1996 | Sorrentino et al. |
| 5,489,058 A | 2/1996 | Plyley et al. |
| 5,497,933 A | 3/1996 | DeFonzo et al. |
| 5,503,320 A | 4/1996 | Webster et al. |
| 5,509,596 A | 4/1996 | Green et al. |
| 5,529,235 A | 6/1996 | Boiarski et al. |
| 5,535,934 A | 7/1996 | Boiarski et al. |
| 5,540,375 A | 7/1996 | Bolanos et al. |
| 5,542,594 A | 8/1996 | McKean et al. |
| 5,553,765 A | 9/1996 | Knodel et al. |
| 5,560,532 A | 10/1996 | DeFonzo et al. |
| 5,562,241 A | 10/1996 | Knodel et al. |
| 5,564,615 A | 10/1996 | Bishop et al. |
| 5,577,654 A | 11/1996 | Bishop |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,603,443 A | 2/1997 | Clark et al. |
| 5,605,273 A | 2/1997 | Hamblin et al. |
| 5,607,094 A | 3/1997 | Clark et al. |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,634,584 A | 6/1997 | Okorocha et al. |
| 5,636,780 A | 6/1997 | Green et al. |
| 5,639,008 A | 6/1997 | Gallagher et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,680,983 A * | 10/1997 | Plyley et al. ............... 227/175.3 |
| 5,690,269 A | 11/1997 | Bolanos et al. |
| 5,692,668 A | 12/1997 | Schulze et al. |
| 5,697,543 A | 12/1997 | Burdorff |
| 5,704,534 A | 1/1998 | Huitema et al. |
| 5,711,472 A | 1/1998 | Bryan |
| 5,715,987 A | 2/1998 | Kelley et al. |
| 5,732,871 A | 3/1998 | Clark et al. |
| 5,732,872 A | 3/1998 | Bolduc et al. |
| 5,743,456 A | 4/1998 | Jones et al. |
| 5,752,644 A | 5/1998 | Bolanos et al. |
| 5,752,965 A | 5/1998 | Francis et al. |
| 5,758,814 A | 6/1998 | Gallagher et al. |
| 5,762,256 A | 6/1998 | Mastri et al. |
| 5,779,130 A | 7/1998 | Alesi et al. |
| 5,779,132 A | 7/1998 | Knodel et al. |
| 5,782,397 A | 7/1998 | Koukline |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,820,009 A | 10/1998 | Melling et al. |
| 5,826,776 A | 10/1998 | Schulze et al. |
| 5,836,503 A | 11/1998 | Ehrenfels et al. |
| 5,839,639 A | 11/1998 | Sauer et al. |
| 5,855,311 A | 1/1999 | Hamblin et al. |
| 5,865,361 A | 2/1999 | Milliman et al. |
| 5,871,135 A | 2/1999 | Williamson IV et al. |
| 5,901,895 A | 5/1999 | Heaton et al. |
| 5,911,353 A | 6/1999 | Bolanos et al. |
| 5,941,442 A | 8/1999 | Geiste et al. |
| 5,954,259 A | 9/1999 | Viola et al. |
| 6,010,054 A | 1/2000 | Johnson et al. |
| 6,032,849 A | 3/2000 | Mastri et al. |
| 6,102,271 A | 8/2000 | Longo et al. |
| 6,119,913 A | 9/2000 | Adams et al. |
| 6,126,058 A | 10/2000 | Adams et al. |
| 6,202,914 B1 | 3/2001 | Geiste et al. |
| 6,241,139 B1 * | 6/2001 | Milliman et al. ......... 227/175.1 |
| 6,250,532 B1 | 6/2001 | Green et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,302,311 B1 | 10/2001 | Adams et al. |
| 6,315,184 B1 | 11/2001 | Whitman |
| 6,325,810 B1 | 12/2001 | Hamilton et al. |
| 6,330,965 B1 | 12/2001 | Milliman et al. |
| 6,488,197 B1 | 12/2002 | Whitman |
| 6,491,201 B1 | 12/2002 | Whitman |
| 6,505,768 B2 | 1/2003 | Whitman |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,619,529 B2 | 9/2003 | Green et al. |
| 6,644,532 B2 | 11/2003 | Green et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,755,338 B2 | 6/2004 | Hahnen et al. |
| 6,786,382 B1 | 9/2004 | Hoffman |
| 6,805,273 B2 | 10/2004 | Bilotti et al. |
| 6,817,508 B1 | 11/2004 | Racenet et al. |
| 6,817,509 B2 * | 11/2004 | Geiste et al. ............... 227/176.1 |
| 6,830,174 B2 | 12/2004 | Hillstead et al. |
| 6,843,403 B2 | 1/2005 | Whitman |
| RE38,708 E | 3/2005 | Bolanos et al. |
| 6,877,647 B2 | 4/2005 | Green et al. |
| 6,905,057 B2 | 6/2005 | Swayze et al. |
| 6,939,358 B2 | 9/2005 | Palacios et al. |
| 6,945,444 B2 | 9/2005 | Gresham et al. |

| | | | | | | |
|---|---|---|---|---|---|---|
| 6,953,138 B1 | 10/2005 | Dworak et al. | | 2005/0189397 A1 | 9/2005 | Jankowski |
| 6,953,139 B2 | 10/2005 | Milliman et al. | | 2005/0263563 A1 | 12/2005 | Racenet et al. |
| 6,964,363 B2 | 11/2005 | Wales et al. | | 2005/0274768 A1 | 12/2005 | Cummins et al. |
| 6,978,921 B2 | 12/2005 | Shelton, IV et al. | | 2006/0011699 A1 | 1/2006 | Olson et al. |
| 6,978,922 B2 | 12/2005 | Bilotti et al. | | 2006/0049229 A1 | 3/2006 | Milliman et al. |
| 6,981,628 B2 | 1/2006 | Wales | | 2006/0173470 A1 | 8/2006 | Oray et al. |
| 6,986,451 B1 | 1/2006 | Mastri et al. | | 2006/0180634 A1 | 8/2006 | Shelton, IV et al. |
| 6,988,650 B2 | 1/2006 | Schwemberger et al. | | 2006/0226196 A1 | 10/2006 | Hueil et al. |
| 7,000,818 B2 | 2/2006 | Shelton, IV et al. | | 2006/0273135 A1 | 12/2006 | Beetel |
| 7,000,819 B2 | 2/2006 | Swayze et al. | | 2006/0278680 A1 | 12/2006 | Viola et al. |
| 7,032,798 B2 | 4/2006 | Whitman et al. | | 2006/0278681 A1 | 12/2006 | Viola et al. |
| 7,032,799 B2 | 4/2006 | Viola et al. | | 2006/0289602 A1 | 12/2006 | Wales et al. |
| 7,044,352 B2 | 5/2006 | Shelton, IV et al. | | 2007/0023477 A1 | 2/2007 | Whitman et al. |
| 7,044,353 B2 | 5/2006 | Mastri et al. | | 2007/0045379 A1 | 3/2007 | Shelton, IV |
| 7,055,730 B2 | 6/2006 | Ehrenfels et al. | | 2007/0073340 A1 | 3/2007 | Shelton, IV et al. |
| 7,055,731 B2 | 6/2006 | Shelton, IV et al. | | 2007/0083234 A1 | 4/2007 | Shelton, IV et al. |
| 7,070,083 B2 | 7/2006 | Jankowski | | 2007/0084897 A1 | 4/2007 | Shelton, IV et al. |
| 7,080,769 B2 | 7/2006 | Vresh et al. | | 2007/0102452 A1 | 5/2007 | Shelton, IV et al. |
| 7,083,075 B2 | 8/2006 | Swayze et al. | | 2007/0102453 A1 | 5/2007 | Morgan et al. |
| 7,111,769 B2 | 9/2006 | Wales et al. | | 2007/0102472 A1 | 5/2007 | Shelton, IV |
| 7,114,642 B2 | 10/2006 | Whitman | | 2007/0102473 A1 | 5/2007 | Shelton, IV et al. |
| 7,128,253 B2 | 10/2006 | Mastri et al. | | 2007/0102474 A1 | 5/2007 | Shelton, IV et al. |
| 7,140,527 B2 * | 11/2006 | Ehrenfels et al. ......... 227/175.1 | | 2007/0106317 A1 | 5/2007 | Shelton, IV et al. |
| 7,147,138 B2 | 12/2006 | Shelton, IV | | 2007/0114261 A1 | 5/2007 | Ortiz et al. |
| 7,159,750 B2 | 1/2007 | Racenet et al. | | 2007/0158385 A1 | 7/2007 | Hueil et al. |
| 7,168,604 B2 | 1/2007 | Milliman et al. | | 2007/0170225 A1 | 7/2007 | Shelton, IV et al. |
| 7,172,104 B2 * | 2/2007 | Scirica et al. ............. 227/175.2 | | 2007/0175949 A1 | 8/2007 | Shelton, IV et al. |
| 7,188,758 B2 | 3/2007 | Viola et al. | | 2007/0175950 A1 | 8/2007 | Shelton, IV et al. |
| 7,210,609 B2 | 5/2007 | Leiboff et al. | | 2007/0175951 A1 | 8/2007 | Shelton, IV et al. |
| 7,213,736 B2 | 5/2007 | Wales et al. | | 2007/0175953 A1 | 8/2007 | Shelton, IV et al. |
| 7,225,964 B2 | 6/2007 | Mastri et al. | | 2007/0175955 A1 | 8/2007 | Shelton, IV et al. |
| 7,246,734 B2 | 7/2007 | Shelton, IV | | 2007/0175956 A1 | 8/2007 | Swayze et al. |
| 7,258,262 B2 | 8/2007 | Mastri et al. | | 2007/0175957 A1 | 8/2007 | Shelton, IV et al. |
| 7,278,563 B1 | 10/2007 | Green | | 2007/0175958 A1 | 8/2007 | Shelton, IV et al. |
| 7,296,724 B2 | 11/2007 | Green et al. | | 2007/0175959 A1 | 8/2007 | Shelton, IV et al. |
| 7,303,106 B2 | 12/2007 | Milliman et al. | | 2007/0175960 A1 | 8/2007 | Shelton, IV et al. |
| 7,303,107 B2 * | 12/2007 | Milliman et al. ......... 227/176.1 | | 2007/0175961 A1 | 8/2007 | Shelton, IV et al. |
| 7,328,828 B2 | 2/2008 | Ortiz et al. | | 2007/0175964 A1 | 8/2007 | Shelton, IV et al. |
| 7,328,829 B2 | 2/2008 | Arad et al. | | 2007/0179476 A1 | 8/2007 | Shelton, IV et al. |
| 7,354,447 B2 | 4/2008 | Shelton, IV et al. | | 2007/0194079 A1 | 8/2007 | Hueil et al. |
| 7,364,061 B2 | 4/2008 | Swayze et al. | | 2007/0194080 A1 | 8/2007 | Swayze et al. |
| 7,380,695 B2 | 6/2008 | Doll et al. | | 2007/0194081 A1 | 8/2007 | Hueil et al. |
| 7,380,696 B2 | 6/2008 | Shelton, IV et al. | | 2007/0194082 A1 | 8/2007 | Morgan et al. |
| 7,398,907 B2 | 7/2008 | Racenet et al. | | 2007/0233053 A1 | 10/2007 | Shelton, IV et al. |
| 7,398,908 B2 | 7/2008 | Holsten et al. | | 2007/0246505 A1 | 10/2007 | Pace-Floridia et al. |
| 7,404,508 B2 | 7/2008 | Smith et al. | | 2007/0262116 A1 | 11/2007 | Hueil et al. |
| 7,404,509 B2 | 7/2008 | Ortiz et al. | | 2007/0295780 A1 | 12/2007 | Shelton et al. |
| 7,407,075 B2 | 8/2008 | Holsten et al. | | 2008/0029570 A1 | 2/2008 | Shelton et al. |
| 7,407,078 B2 | 8/2008 | Shelton, IV et al. | | 2008/0029571 A1 | 2/2008 | Shelton et al. |
| 7,410,086 B2 | 8/2008 | Ortiz et al. | | 2008/0029572 A1 | 2/2008 | Shelton et al. |
| 7,416,101 B2 | 8/2008 | Shelton, IV et al. | | 2008/0029573 A1 | 2/2008 | Shelton et al. |
| 7,422,136 B1 | 9/2008 | Marczyk | | 2008/0029574 A1 | 2/2008 | Shelton et al. |
| 7,422,139 B2 | 9/2008 | Shelton, IV et al. | | 2008/0029575 A1 | 2/2008 | Shelton et al. |
| 7,424,965 B2 | 9/2008 | Racenet et al. | | 2008/0029576 A1 | 2/2008 | Shelton et al. |
| 7,431,188 B1 | 10/2008 | Marczyk | | 2008/0029577 A1 | 2/2008 | Shelton et al. |
| 7,438,209 B1 | 10/2008 | Hess et al. | | 2008/0035701 A1 | 2/2008 | Racenet et al. |
| 7,441,685 B1 | 10/2008 | Boudreaux | | 2008/0041917 A1 | 2/2008 | Racenet et al. |
| 7,481,347 B2 | 1/2009 | Roy | | 2008/0078800 A1 | 4/2008 | Hess et al. |
| 7,490,749 B2 | 2/2009 | Schall et al. | | 2008/0078801 A1 | 4/2008 | Shelton et al. |
| 7,494,039 B2 | 2/2009 | Racenet et al. | | 2008/0078802 A1 | 4/2008 | Hess et al. |
| 7,506,790 B2 | 3/2009 | Shelton, IV | | 2008/0078803 A1 | 4/2008 | Shelton et al. |
| 7,510,107 B2 | 3/2009 | Timm et al. | | 2008/0078804 A1 | 4/2008 | Shelton et al. |
| 7,546,940 B2 | 6/2009 | Milliman et al. | | 2008/0078805 A1 | 4/2008 | Omaits et al. |
| 7,549,564 B2 | 6/2009 | Boudreaux | | 2008/0078806 A1 | 4/2008 | Omaits et al. |
| 2002/0117534 A1 | 8/2002 | Green et al. | | 2008/0078807 A1 | 4/2008 | Hess et al. |
| 2004/0094597 A1 | 5/2004 | Whitman et al. | | 2008/0078808 A1 | 4/2008 | Hess et al. |
| 2004/0108357 A1 | 6/2004 | Milliman et al. | | 2008/0082115 A1 | 4/2008 | Morgan et al. |
| 2004/0164123 A1 | 8/2004 | Racenet et al. | | 2008/0082124 A1 | 4/2008 | Hess et al. |
| 2004/0173659 A1 | 9/2004 | Green et al. | | 2008/0082125 A1 | 4/2008 | Murray et al. |
| 2004/0222268 A1 | 11/2004 | Bilotti et al. | | 2008/0082126 A1 | 4/2008 | Murray et al. |
| 2004/0232201 A1 | 11/2004 | Wenchell et al. | | 2008/0164296 A1 | 7/2008 | Shelton et al. |
| 2005/0103819 A1 | 5/2005 | Racenet et al. | | 2008/0167522 A1 | 7/2008 | Giordano et al. |
| 2005/0184121 A1 | 8/2005 | Heinrich | | 2008/0167644 A1 | 7/2008 | Shelton et al. |

| | | | | | | |
|---|---|---|---|---|---|---|
| 2008/0167670 A1 | 7/2008 | Shelton et al. | | 2009/0289096 A1 | 11/2009 | Shelton, IV et al. |
| 2008/0167671 A1 | 7/2008 | Giordano et al. | | | | |
| 2008/0167672 A1 | 7/2008 | Giordano et al. | | FOREIGN PATENT DOCUMENTS | | |
| 2008/0167736 A1 | 7/2008 | Swayze et al. | | | | |
| 2008/0169327 A1 | 7/2008 | Shelton et al. | | CA | 2512960 A1 | 1/2006 |
| 2008/0169328 A1 | 7/2008 | Shelton | | CA | 2514274 A1 | 1/2006 |
| 2008/0169329 A1 | 7/2008 | Shelton et al. | | DE | 273689 C | 5/1914 |
| 2008/0169330 A1 | 7/2008 | Shelton et al. | | DE | 1775926 A | 1/1972 |
| 2008/0169331 A1 | 7/2008 | Shelton et al. | | DE | 9412228 U | 9/1994 |
| 2008/0169332 A1 | 7/2008 | Shelton et al. | | DE | 19924311 A1 | 11/2000 |
| 2008/0169333 A1 | 7/2008 | Shelton et al. | | DE | 69328576 T2 | 1/2001 |
| 2008/0210738 A1 | 9/2008 | Shelton et al. | | DE | 20112837 U1 | 10/2001 |
| 2008/0237296 A1 | 10/2008 | Boudreaux et al. | | DE | 20121753 U1 | 4/2003 |
| 2008/0251568 A1 | 10/2008 | Zemlok et al. | | DE | 10314072 A1 | 10/2004 |
| 2008/0296343 A1 | 12/2008 | Schall et al. | | EP | 0122046 A1 | 10/1984 |
| 2008/0296345 A1 | 12/2008 | Shelton, IV et al. | | EP | 0033548 B1 | 5/1986 |
| 2008/0296346 A1 | 12/2008 | Shelton, IV et al. | | EP | 0276104 A2 | 7/1988 |
| 2008/0296347 A1 | 12/2008 | Shelton, IV et al. | | EP | 0639349 A2 | 2/1994 |
| 2008/0300579 A1 | 12/2008 | Broehl et al. | | EP | 0324636 B1 | 3/1994 |
| 2008/0300580 A1 | 12/2008 | Shelton, IV et al. | | EP | 0593920 A1 | 4/1994 |
| 2008/0300613 A1 | 12/2008 | Shelton, IV et al. | | EP | 0600182 A2 | 6/1994 |
| 2008/0308601 A1 | 12/2008 | Timm et al. | | EP | 0630612 A1 | 12/1994 |
| 2008/0308602 A1 | 12/2008 | Timm et al. | | EP | 0634144 A1 | 1/1995 |
| 2008/0308603 A1 | 12/2008 | Shelton, IV et al. | | EP | 0646356 A2 | 4/1995 |
| 2008/0308606 A1 | 12/2008 | Timm et al. | | EP | 0646357 A1 | 4/1995 |
| 2008/0308607 A1 | 12/2008 | Timm et al. | | EP | 0653189 A2 | 5/1995 |
| 2008/0308608 A1 | 12/2008 | Prommersberger | | EP | 0669104 A1 | 8/1995 |
| 2008/0314954 A1 | 12/2008 | Boudreaux | | EP | 0679367 A2 | 11/1995 |
| 2008/0314955 A1 | 12/2008 | Boudreaux et al. | | EP | 0392547 B1 | 12/1995 |
| 2008/0314957 A1 | 12/2008 | Boudreaux | | EP | 0685204 A1 | 12/1995 |
| 2008/0314960 A1 | 12/2008 | Marczyk et al. | | EP | 0699418 A1 | 3/1996 |
| 2008/0314961 A1 | 12/2008 | Boudreaux et al. | | EP | 0702937 A1 | 3/1996 |
| 2008/0314962 A1 | 12/2008 | Boudreaux | | EP | 0705571 A1 | 4/1996 |
| 2009/0001121 A1 | 1/2009 | Hess et al. | | EP | 0484677 B2 | 6/1996 |
| 2009/0001123 A1 | 1/2009 | Morgan et al. | | EP | 0541987 B1 | 7/1996 |
| 2009/0001124 A1 | 1/2009 | Hess et al. | | EP | 0667119 B1 | 7/1996 |
| 2009/0001125 A1 | 1/2009 | Hess et al. | | EP | 0770355 A1 | 5/1997 |
| 2009/0001126 A1 | 1/2009 | Hess et al. | | EP | 0503662 B1 | 6/1997 |
| 2009/0001128 A1 | 1/2009 | Weisenburgh, II et al. | | EP | 0578425 B1 | 9/1997 |
| 2009/0001130 A1 | 1/2009 | Hess et al. | | EP | 0625335 B1 | 11/1997 |
| 2009/0005807 A1 | 1/2009 | Hess et al. | | EP | 0552423 B1 | 1/1998 |
| 2009/0005808 A1 | 1/2009 | Hess et al. | | EP | 0592244 B1 | 1/1998 |
| 2009/0005809 A1 | 1/2009 | Hess et al. | | EP | 0648476 B1 | 1/1998 |
| 2009/0012556 A1 | 1/2009 | Boudreaux et al. | | EP | 0676173 B1 | 9/1998 |
| 2009/0076534 A1 | 3/2009 | Shelton, IV et al. | | EP | 0603472 B1 | 11/1998 |
| 2009/0206123 A1 | 8/2009 | Doll et al. | | EP | 0605351 B1 | 11/1998 |
| 2009/0206124 A1 | 8/2009 | Hall et al. | | EP | 0878169 A1 | 11/1998 |
| 2009/0206125 A1 | 8/2009 | Huitema et al. | | EP | 0879742 A1 | 11/1998 |
| 2009/0206126 A1 | 8/2009 | Huitema et al. | | EP | 0760230 B1 | 2/1999 |
| 2009/0206128 A1 | 8/2009 | Hueil et al. | | EP | 0537572 B1 | 6/1999 |
| 2009/0206129 A1 | 8/2009 | Doll et al. | | EP | 0552050 B1 | 5/2000 |
| 2009/0206130 A1 | 8/2009 | Hall et al. | | EP | 1090592 A1 | 4/2001 |
| 2009/0206131 A1 | 8/2009 | Weisenburgh, II et al. | | EP | 1256318 B1 | 5/2001 |
| 2009/0206132 A1 | 8/2009 | Hueil et al. | | EP | 0908152 B1 | 1/2002 |
| 2009/0206133 A1 | 8/2009 | Morgan et al. | | EP | 0872213 B1 | 5/2002 |
| 2009/0206134 A1 | 8/2009 | Swayze et al. | | EP | 1238634 A2 | 9/2002 |
| 2009/0206135 A1 | 8/2009 | Hall et al. | | EP | 0656188 B1 | 1/2003 |
| 2009/0206136 A1 | 8/2009 | Moore et al. | | EP | 0829235 B1 | 6/2003 |
| 2009/0206137 A1 | 8/2009 | Hall et al. | | EP | 0813843 B1 | 10/2003 |
| 2009/0206138 A1 | 8/2009 | Smith et al. | | EP | 0741996 B1 | 2/2004 |
| 2009/0206139 A1 | 8/2009 | Hall et al. | | EP | 0705570 B1 | 4/2004 |
| 2009/0206140 A1 | 8/2009 | Scheib et al. | | EP | 1086713 B1 | 5/2004 |
| 2009/0206141 A1 | 8/2009 | Huitema et al. | | EP | 1426012 A1 | 6/2004 |
| 2009/0206142 A1 | 8/2009 | Huitema et al. | | EP | 0888749 B1 | 9/2004 |
| 2009/0206143 A1 | 8/2009 | Huitema et al. | | EP | 1477119 A1 | 11/2004 |
| 2009/0206144 A1 | 8/2009 | Doll et al. | | EP | 1479345 A1 | 11/2004 |
| 2009/0209946 A1 | 8/2009 | Swayze et al. | | EP | 1479347 A1 | 11/2004 |
| 2009/0255974 A1 | 10/2009 | Viola | | EP | 1479348 A1 | 11/2004 |
| 2009/0255975 A1 | 10/2009 | Zemlok et al. | | EP | 1520521 A1 | 4/2005 |
| 2009/0255976 A1 | 10/2009 | Marczyk et al. | | EP | 1520523 A1 | 4/2005 |
| 2009/0255977 A1 | 10/2009 | Zemlok | | EP | 1520525 A1 | 4/2005 |
| 2009/0255978 A1 | 10/2009 | Viola et al. | | EP | 1522264 A1 | 4/2005 |
| | | | | EP | 1550408 A1 | 7/2005 |

| | | | | | | | |
|---|---|---|---|---|---|---|---|
| EP | 1557129 | A1 | 7/2005 | WO | WO 01/05702 | A1 | 1/2001 |
| EP | 1064883 | B1 | 8/2005 | WO | WO 01/10482 | A1 | 2/2001 |
| EP | 1157666 | B1 | 9/2005 | WO | WO 01/54594 | A1 | 8/2001 |
| EP | 1621138 | A2 | 2/2006 | WO | WO 01/62158 | A2 | 8/2001 |
| EP | 1621139 | A2 | 2/2006 | WO | WO 01/62162 | A1 | 8/2001 |
| EP | 1621141 | A2 | 2/2006 | WO | WO 01/62164 | A2 | 8/2001 |
| EP | 1621145 | A2 | 2/2006 | WO | WO 01/91646 | A1 | 12/2001 |
| EP | 1652481 | A2 | 5/2006 | WO | WO 02/07608 | A2 | 1/2002 |
| EP | 1382303 | B1 | 6/2006 | WO | WO 02/07618 | A1 | 1/2002 |
| EP | 1045672 | B1 | 8/2006 | WO | WO 02/17799 | A1 | 3/2002 |
| EP | 1617768 | B1 | 8/2006 | WO | WO 02/19920 | A1 | 3/2002 |
| EP | 1702567 | A2 | 9/2006 | WO | WO 02/30297 | A2 | 4/2002 |
| EP | 1129665 | B1 | 11/2006 | WO | WO 02/32322 | A2 | 4/2002 |
| EP | 1256317 | B1 | 12/2006 | WO | WO 02/43571 | A2 | 6/2002 |
| EP | 1728473 | A1 | 12/2006 | WO | WO 02/058568 | A1 | 8/2002 |
| EP | 1728475 | A2 | 12/2006 | WO | WO 02/067785 | A2 | 9/2002 |
| EP | 1479346 | B1 | 1/2007 | WO | WO 02/098302 | A2 | 12/2002 |
| EP | 1484024 | B1 | 1/2007 | WO | WO 03/000138 | A2 | 1/2003 |
| EP | 1754445 | A2 | 2/2007 | WO | WO 03/001329 | A2 | 1/2003 |
| EP | 1759812 | A1 | 3/2007 | WO | WO 03/013363 | A1 | 2/2003 |
| EP | 1769756 | A1 | 4/2007 | WO | WO 03/020106 | A2 | 3/2003 |
| EP | 1769758 | A1 | 4/2007 | WO | WO 03/079909 | A3 | 3/2003 |
| EP | 1785097 | A2 | 5/2007 | WO | WO 03/030743 | A2 | 4/2003 |
| EP | 1790293 | A2 | 5/2007 | WO | WO 03/037193 | A1 | 5/2003 |
| EP | 1300117 | B1 | 8/2007 | WO | WO 03/047436 | A3 | 6/2003 |
| EP | 1813199 | A1 | 8/2007 | WO | WO 03/057048 | A1 | 7/2003 |
| EP | 1813201 | A1 | 8/2007 | WO | WO 03/057058 | A1 | 7/2003 |
| EP | 1813203 | A2 | 8/2007 | WO | WO 03/063694 | A1 | 8/2003 |
| EP | 1813207 | A1 | 8/2007 | WO | WO 03/077769 | A1 | 9/2003 |
| EP | 1813209 | A1 | 8/2007 | WO | WO 03/082126 | A1 | 10/2003 |
| EP | 1839596 | A1 | 10/2007 | WO | WO 03/088845 | A2 | 10/2003 |
| EP | 1872727 | A1 | 1/2008 | WO | WO 03/090630 | A2 | 11/2003 |
| EP | 1897502 | A1 | 3/2008 | WO | WO 03/094743 | A1 | 11/2003 |
| EP | 1702568 | B1 | 7/2008 | WO | WO 03/094745 | A1 | 11/2003 |
| EP | 1759645 | B1 | 11/2008 | WO | WO 03/094746 | A1 | 11/2003 |
| EP | 1749486 | B1 | 3/2009 | WO | WO 03/094747 | A1 | 11/2003 |
| FR | 999646 | A | 2/1952 | WO | WO 03/101313 | A1 | 12/2003 |
| FR | 1112936 | A | 3/1956 | WO | WO 03/105698 | A2 | 12/2003 |
| FR | 2765794 | A | 1/1999 | WO | WO 03/105702 | A2 | 12/2003 |
| GB | 939929 | A | 10/1963 | WO | WO 2004/006980 | A2 | 1/2004 |
| GB | 1210522 | A | 10/1970 | WO | WO 2004/028585 | A2 | 4/2004 |
| GB | 2336214 | A | 10/1999 | WO | WO 2004/032754 | A2 | 4/2004 |
| JP | 6007357 | A | 1/1994 | WO | WO 2004/032760 | A2 | 4/2004 |
| JP | 7051273 | A | 2/1995 | WO | WO 2004/032762 | A1 | 4/2004 |
| JP | 8033641 | A | 2/1996 | WO | WO 2004/032763 | A2 | 4/2004 |
| JP | 8229050 | A | 9/1996 | WO | WO 2004/047653 | A2 | 6/2004 |
| JP | 2000287987 | A | 10/2000 | WO | WO 2004/049956 | A2 | 6/2004 |
| JP | 2001286477 | A | 10/2001 | WO | WO 2004/086987 | A1 | 10/2004 |
| JP | 2002369820 | A | 12/2002 | WO | WO 2004/096057 | A2 | 11/2004 |
| JP | 2005505322 | T | 2/2005 | WO | WO 2004/105621 | A1 | 12/2004 |
| JP | 2005103293 | A | 4/2005 | WO | WO 2004/112618 | A2 | 12/2004 |
| RU | 2187249 | C2 | 8/2002 | WO | WO 2004/112652 | A2 | 12/2004 |
| RU | 2225170 | C2 | 3/2004 | WO | WO 2005/027983 | A2 | 3/2005 |
| SU | 1377053 | A1 | 2/1988 | WO | WO 2005/037329 | A2 | 4/2005 |
| SU | 1561964 | A1 | 5/1990 | WO | WO 2005/078892 | A1 | 8/2005 |
| SU | 1722476 | A1 | 3/1992 | WO | WO 2005/096954 | A2 | 10/2005 |
| WO | WO 93/08755 | A1 | 5/1993 | WO | WO 2005/112808 | A1 | 12/2005 |
| WO | WO 95/18572 | A1 | 7/1995 | WO | WO 2005/115251 | A2 | 12/2005 |
| WO | WO 95/23557 | A1 | 9/1995 | WO | WO 2006/044490 | A2 | 4/2006 |
| WO | WO 95/29639 | A1 | 11/1995 | WO | WO 2006/044581 | A2 | 4/2006 |
| WO | WO 96/35464 | A1 | 11/1996 | WO | WO 2006/044810 | A2 | 4/2006 |
| WO | WO 97/34533 | A1 | 9/1997 | WO | WO 2006/083748 | A1 | 8/2006 |
| WO | WO 97/39688 | A2 | 10/1997 | WO | WO 2006/115958 | A1 | 11/2006 |
| WO | WO 98/30153 | A1 | 7/1998 | WO | WO 2006/132992 | A1 | 12/2006 |
| WO | WO 99/12483 | A1 | 3/1999 | WO | WO 2007/016290 | A2 | 2/2007 |
| WO | WO 99/15086 | A1 | 4/1999 | WO | WO 2007/018898 | A2 | 2/2007 |
| WO | WO 99/34744 | A1 | 7/1999 | WO | WO 2007/121579 | A1 | 11/2007 |
| WO | WO 99/45849 | A1 | 9/1999 | WO | WO 2007/139734 | A2 | 12/2007 |
| WO | WO 00/24322 | A1 | 5/2000 | WO | WO 2007/142625 | A2 | 12/2007 |
| WO | WO 00/57796 | A1 | 10/2000 | WO | WO 2008/039270 | A1 | 4/2008 |
| WO | WO 00/64365 | A1 | 11/2000 | | | | |
| WO | WO 00/72762 | A1 | 12/2000 | | | | |
| WO | WO 00/72765 | A1 | 12/2000 | | | | |

| | | |
|---|---|---|
| WO | WO 2008/045383 A2 | 4/2008 |

OTHER PUBLICATIONS

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

* cited by examiner

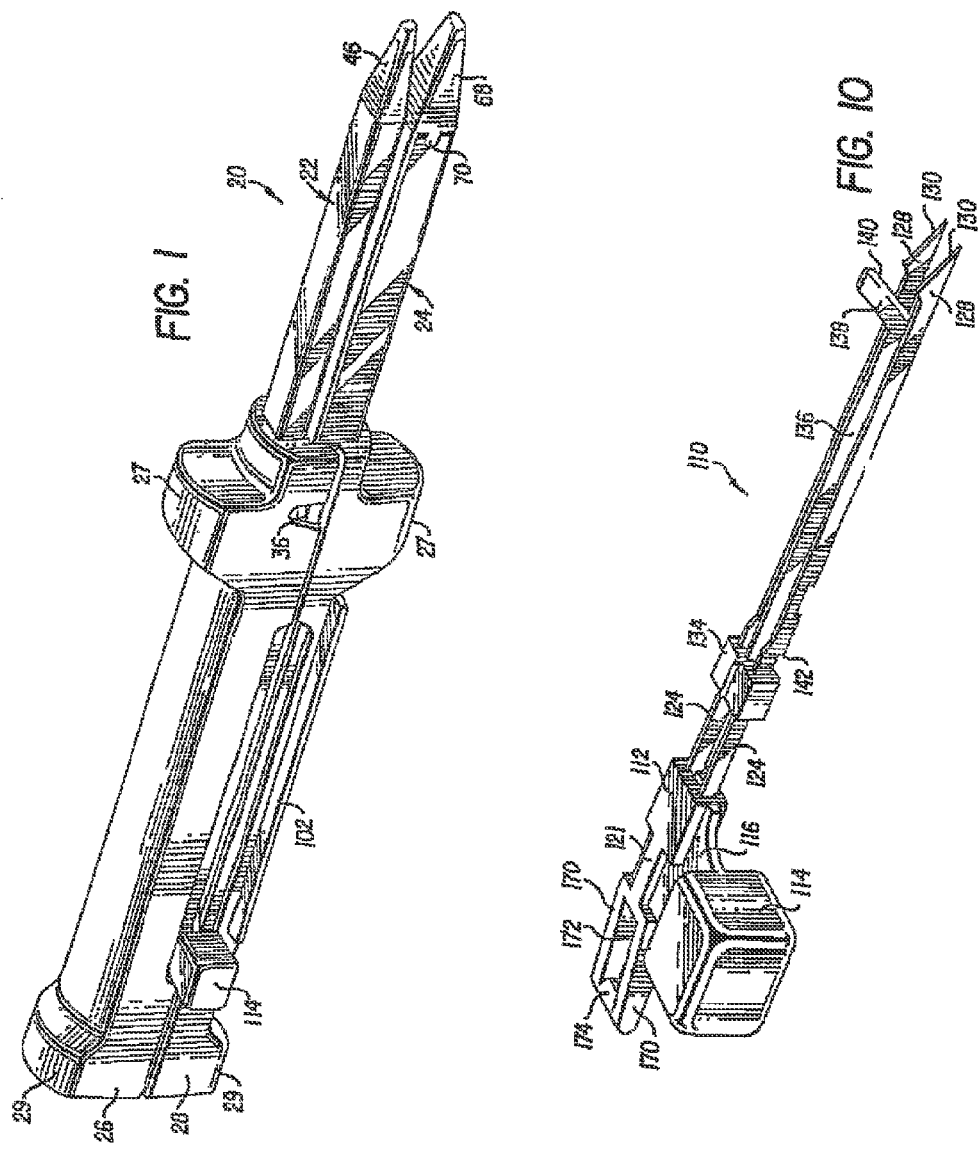

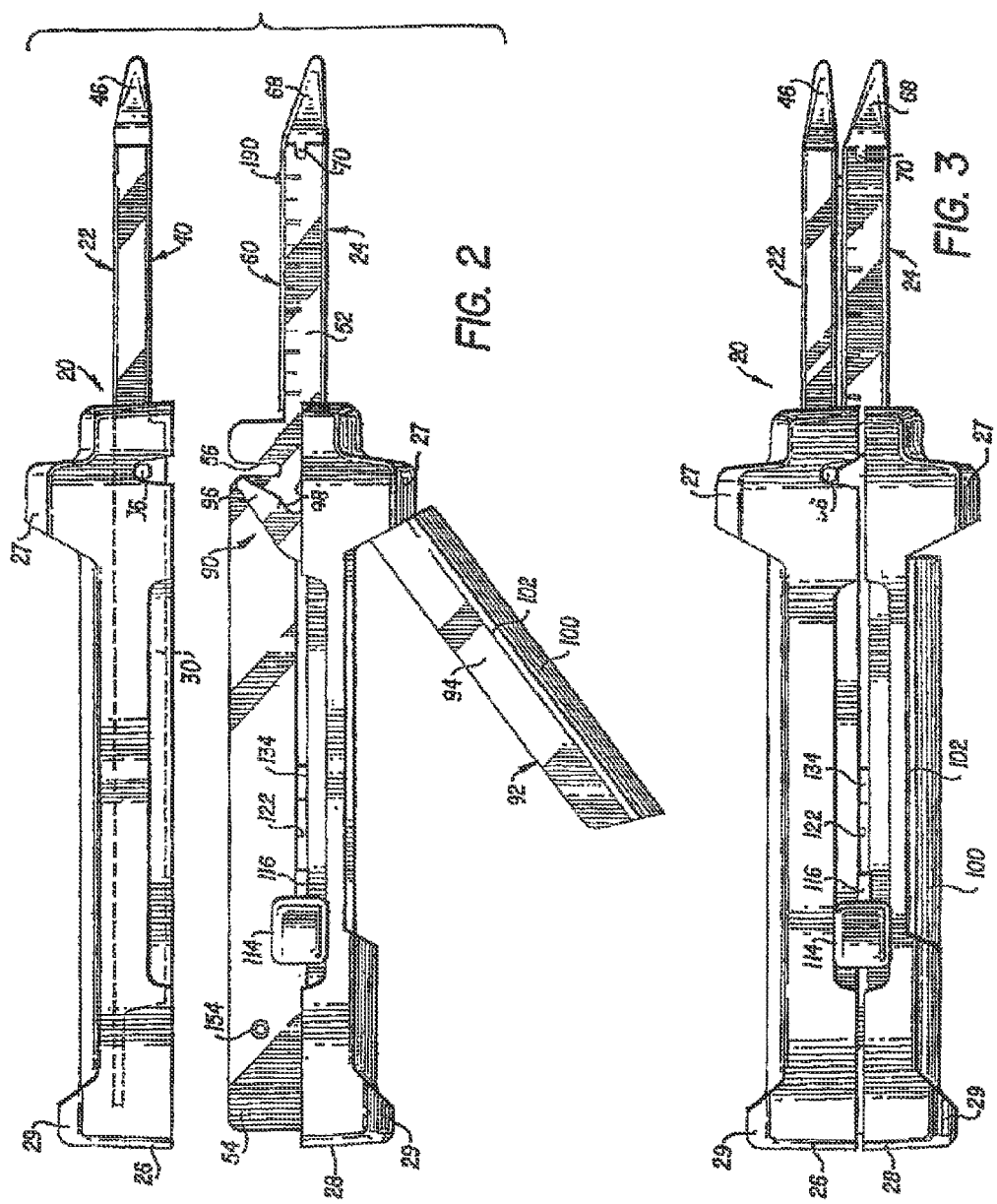

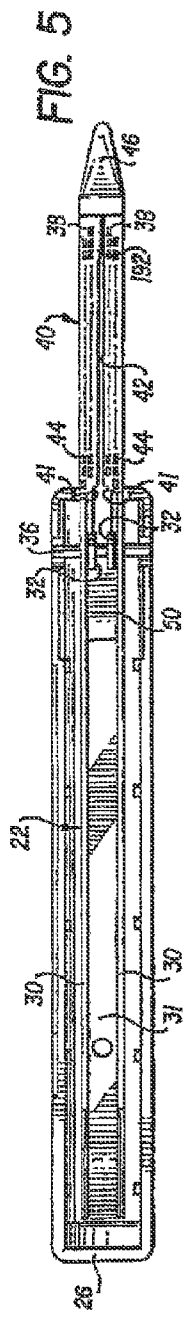
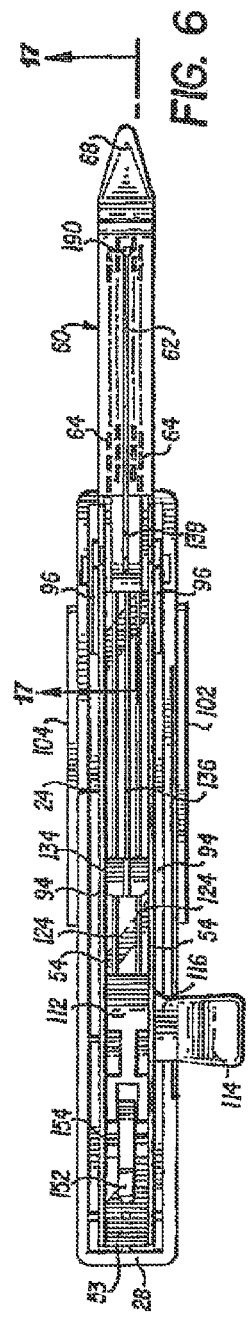
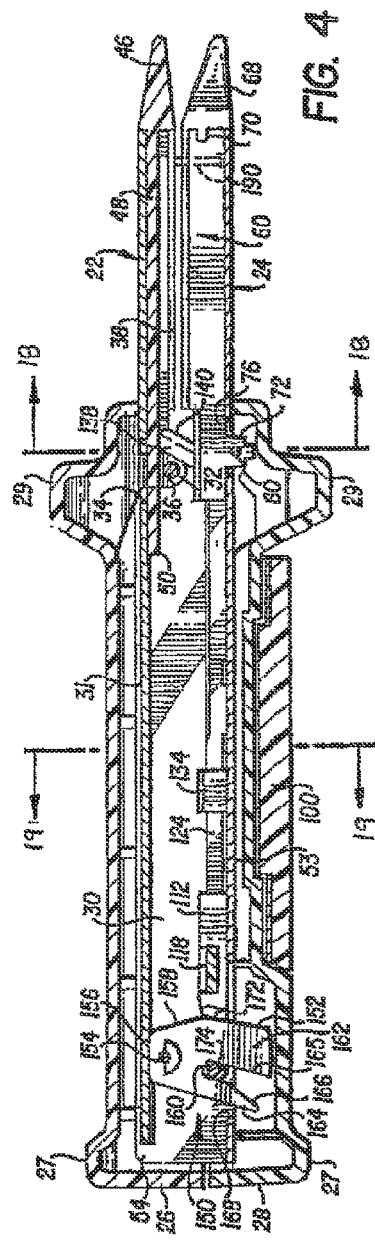

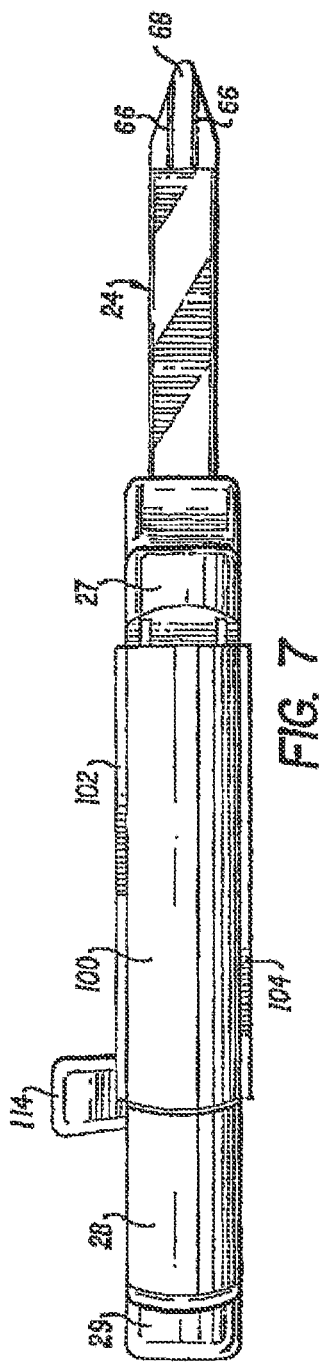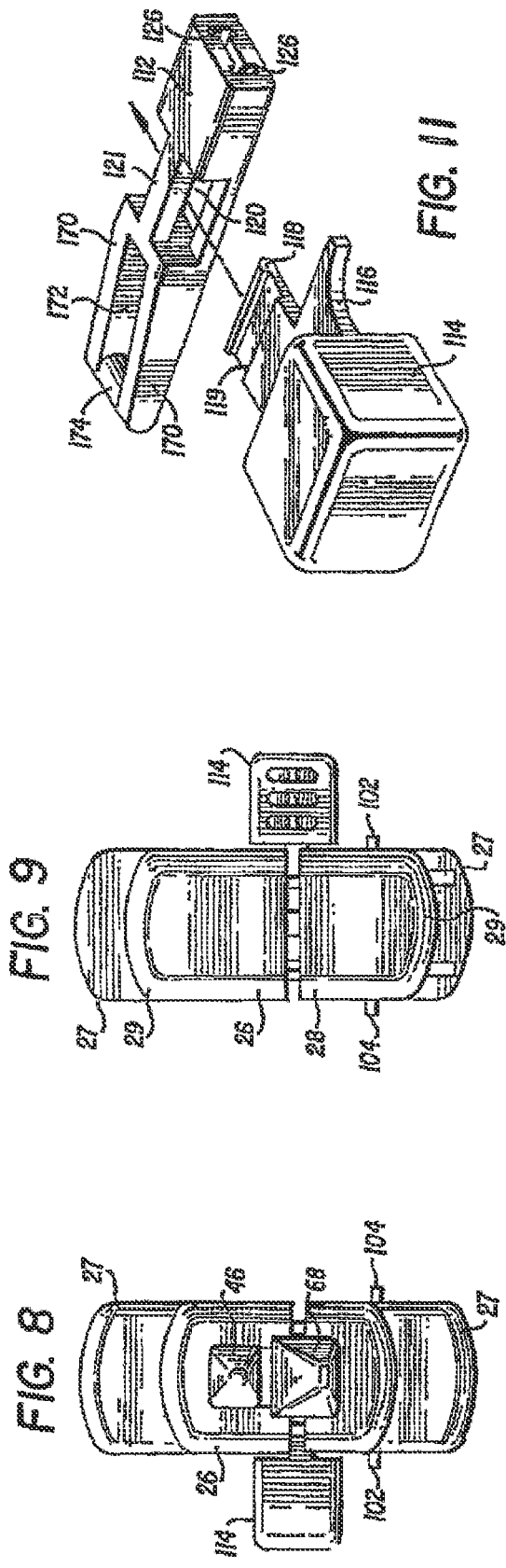

SURGICAL STAPLING INSTRUMENT WITH IMPROVED FIRING TRIGGER ARRANGEMENT

BACKGROUND i. Technical Field

The present invention relates to a surgical stapling instrument and, in various embodiments, to a gastrointestinal anastomotic stapling instrument for producing one or more rows of staples.

ii. Background of the Related Art

In recent years, there has been an increasing tendency for surgeons to use stapling instruments to suture body tissues such as a lung, an esophagus, a stomach, a duodenum and/or other organs in the intestinal tract. The use of an appropriate stapling instrument in many instances may perform a better job in less time and simplify previously difficult surgical procedures such as gastrointestinal anastomoses. Previous linear two and four row cutting staplers comprised cartridgeless instruments into which staples were individually handloaded. Other previous devices have included a presterilized disposable staple loading unit and a cutting member which could be utilized for dividing the tissue and forming the rows of staples simultaneously. An example of such a surgical stapler is disclosed in U.S. Pat. No. 3,499,591, the entire disclosure of which is hereby incorporated by reference herein.

A linear anastomotic stapling instrument can include a pair of cooperating elongate jaw members, wherein each jaw member can be adapted to be inserted into an internal, tubular body organ to be anastomosed. In various embodiments, one of the jaw members can support a staple cartridge with at least two laterally spaced rows of staples, and the other jaw member can support an anvil with staple-forming pockets aligned with the rows of staples in the staple cartridge. Generally, the stapling instrument can further include a pusher bar and knife blade assembly which is slidable relative to the jaw members to sequentially eject staples from the staple cartridge via camming surfaces on the pusher bar. In at least one embodiment, the camming surfaces can be configured to activate a plurality of staple drivers carried by the cartridge and associated with the individual staples to push the staples against the anvil and form laterally spaced rows of deformed staples in the tissue gripped between the jaw members. In at least one embodiment, the knife blade can trail the pusher bar and cut the tissue along a line between the staple rows. Examples of such anastomotic stapling instruments are disclosed in U.S. Pat. No. 4,429,695, the entire disclosure of which is hereby incorporated by reference herein.

In various circumstances, a linear anastomotic stapling instrument can include an actuator knob extending from the pusher bar which can be configured to be grasped by a surgeon and advanced distally to advance the pusher bar and knife blade assembly within the staple cartridge. In at least one circumstance, though, the actuator knob, as it can extend outwardly from the surgical instrument, can unintentionally contact tissue surrounding the surgical site and, as a result, the tissue may impede the advancement of the actuator knob. In such circumstances, a surgeon may have to force the actuator knob past the tissue and/or re-position the stapling instrument which can increase the time needed to complete the surgery. What is needed is an improvement over the foregoing.

SUMMARY

In at least one form of the present invention, a surgical stapling instrument can include an actuator knob which can be moved from one side of the stapling instrument to another side in order to reposition the actuator knob without having to reposition the stapling instrument within a surgical site. In various embodiments, a stapling instrument can include a staple cartridge having at least two rows of staples stored therein, a pusher bar, a staple driver operably engaged with the pusher bar, wherein the staple driver can be configured to eject the staples from the staple cartridge, and an anvil configured to deform the staples when they are deployed from the staple cartridge. In at least one embodiment, the stapling instrument can further include a housing having a first side and a second side and, in addition, an actuator knob rotatably mounted to the pusher bar wherein the actuator knob can be configured to be rotated between a first position in which the actuator knob can be moved along the first side of the housing and a second position where the actuator knob can be configured to be moved along a second side of the housing.

In at least one form of the present invention, a surgical stapling instrument can comprise one or more actuator knobs which can be operably engaged with and disengaged from a pusher bar in order to selectively utilize the actuator knobs. In various embodiments, a stapling instrument can include one or more rotatable actuator knobs which can be rotated between a first, retracted position in which they are operably disengaged from the pusher bar and a second, extended position in which they are operably engaged with the pusher bar. In at least one embodiment, a surgeon can selectively extend an actuator knob to advance the pusher bar such that the selected actuator knob does not interfere, or at least substantially interfere, with the surrounding tissue. The other actuator knob, or knobs, can remain in a retracted, disengaged position such that they do not have to be advanced with the pusher bar and/or do not substantially extend from the outer perimeter of the surgical stapling instrument.

BRIEF DESCRIPTION OF DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 1 is a perspective view of a linear anastomotic stapling instrument;

FIG. 2 is a side elevational view showing the anastomotic stapling instrument of FIG. 1 partially disassembled with its upper anvil carrying jaw member detached from its lower staple cartridge carrying jaw member;

FIG. 3 is a side elevational view showing the anastomotic stapling instrument of FIG. 1 in its assembled configuration;

FIG. 4 is a cross-sectional view of the anastomotic stapling instrument of FIG. 1 showing a cam mechanism for urging the rear portions of the upper and lower jaw members apart;

FIG. 5 is a bottom view of the anvil carrying jaw member of the anastomotic stapling instrument of FIG. 1;

FIG. 6 is a top view of the staple cartridge carrying jaw member of the anastomotic stapling instrument of FIG. 1;

FIG. 7 is a bottom view of the anastomotic stapling instrument of FIG. 1;

FIG. 8 is a front end view of the anastomotic stapling instrument of FIG. 1;

FIG. 9 is a rear end view of the anastomotic stapling instrument of FIG. 1;

FIG. 10 is a perspective view of a pusher bar and knife blade assembly of the anastomotic stapling instrument of FIG. 1;

FIG. 11 is a perspective view of a pusher block and an actuator knob which are components of the pusher bar and knife blade assembly of FIG. 10;

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Figure 12:
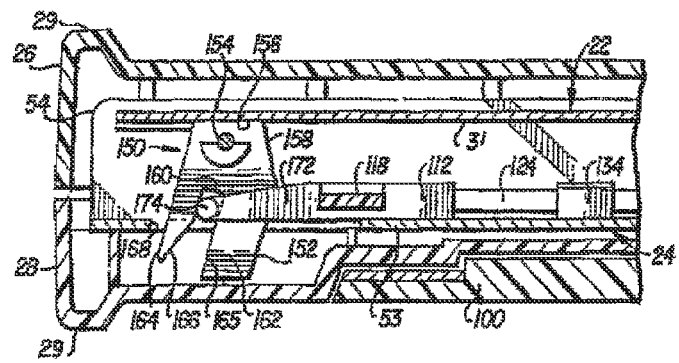
FIG. 12 is a partial cross-sectional view of the rear portion of the anastomotic stapling instrument of FIG. 1 illustrating the cam mechanism in its inoperative position.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Referring to FIGS. 1 and 2, a linear anastomotic stapling instrument, generally 20, can comprise an upper elongated anvil carrying jaw member 22 and a lower elongated staple cartridge carrying jaw member 24. Upper anvil carrying jaw member 22 can be supported by a handle 26 with a front portion of the jaw member extending forwardly therefrom. Lower staple cartridge carrying jaw member 24 can be supported by a handle 28 with a front portion of the jaw member extending forwardly therefrom. As shown in FIG. 3, upper handle 26 and lower handle 28 can be suitably shaped to form a hand grip to facilitate the handling and operation of the stapling instrument by a surgeon. An enlarged front protrusion 27 and a small rear protrusion 29 can be provided on each handle for this purpose. In various embodiments, handles 26 and 28 can be made of plastic of other lightweight materials, for example, while jaw members 22 and 24 can be made of stainless steel or other similar materials, for example.

As shown in FIG. 5, upper jaw member 22 can comprise a one-piece elongated channel-shaped frame including a pair of opposed, elongated side walls 30 connected by a top wall 31. Upper handle 26 can include a pair of depending ears 32 located inside the upper handle adjacent to its front end. Upper jaw member 22 can include a slot 34 (FIG. 4) formed at an intermediate position along its top wall 31 through which depending ears 32 can project downwardly. A latch pin 36 can extend through circular holes formed in side walls 30 of upper jaw member 22 and through circular holes formed in depending ears 32 to pivotally connect the upper jaw member to upper handle 26.

Referring to FIG. 5, the front portion of upper jaw member 22 can be provided with a pair of elongated inwardly extending flanges 38 which can define an anvil 40 of the stapling instrument. Flanges 38 can be separated by a central longitudinal slot 42 which extends along the entire length of anvil 40. At the proximal end of central slot 42, the flanges 38 can be provided with inwardly sloped guide surfaces 41. Each flange 38 can also provided with two longitudinal rows of uniformly spaced staple-forming pockets 44. Referring to FIGS. 4 and 5, a tapered anvil tip 46 can be mounted at the front of anvil carrying jaw member 22 to facilitate the insertion of the jaw member into hollow, tubular body organs, for example. Anvil tip 46 can include an elongated body 48 (FIG. 4) which can be inserted through the longitudinal passageway above anvil 40 defined by side walls 30 and flanges 38 of the upper jaw member. This elongated body 48 can extend between depending ears 32 above latch pin 36 and can include an enlarged rear portion 50 located behind ears 32 to hold anvil tip 46 in place on upper jaw member 22.

Referring to FIGS. 2 and 6, lower cartridge carrying jaw member 24 can comprise a one-piece elongated channel-shaped frame including a pair of opposed, elongated side walls 52 connected by a bottom wall 53. Along the rearward portion of lower jaw member 24, a pair of spaced, elongated upstanding side flanges 54 (FIG. 2) can extend upward from its opposed side walls 52. As shown in FIGS. 5 and 6, the width of lower jaw member 24 between its side flanges 54 can be greater than the width of upper jaw member 22 between its side walls 30 to permit the rear portion of the upper jaw member to be received between side flanges 54 of the lower jaw member when the stapling instrument is assembled for operation. As shown in FIG. 2, each side flange 54 of lower jaw member 24 can include a vertical notch 56 located in alignment with latch pin 36 on upper jaw member 22. When upper jaw member 22 and lower jaw member 24 are assembled, the opposite ends of latch pin 36 can be received in notches 56.

Figure 15:
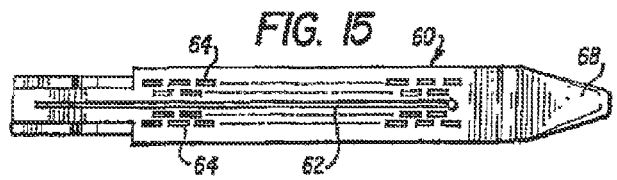
FIG. 15 is a top view of the staple cartridge of the anastomotic stapling instrument of FIG. 1.
Figure 16:
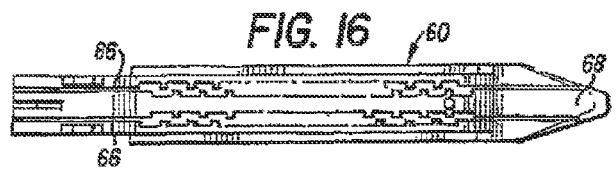
FIG. 16 is a bottom view of the staple cartridge of the anastomotic stapling instrument of FIG. 1.

As shown in FIGS. 2 and 6, lower jaw member 24 can support a staple cartridge 60 which is adapted to receive a plurality of surgical staples 61 (FIG. 17) arranged in at least two laterally spaced longitudinal rows. Staple cartridge 60 can be mounted at the front portion of lower jaw member 24 between its side walls 52. Staple cartridge 60 can be divided longitudinally by a central, elongated slot 62 (FIG. 6) which extends from the proximal end of the cartridge toward its distal end. In various embodiments, a plurality of staple openings 64 formed in staple cartridge 60 can be arranged in two pairs of laterally spaced rows, with each pair of rows disposed on opposite sides of central longitudinal slot 62. A plurality of surgical staples 61 (FIG. 17) can be mounted within openings 64 of cartridge 60. As shown in FIG. 6, the staple openings 64 in adjacent rows can be staggered to provide more effective stapling of the tissue when the instrument is operated. Referring to FIGS. 15 and 16, staple cartridge 60 can include a pair of longitudinal slots 66 located on opposite sides of elongated central slot 62 and disposed between the staggered rows of openings 64 on each side of the central slot. Each longitudinal slot 66 can extend from the proximal end of cartridge 60 towards its distal end.

Figure 17:
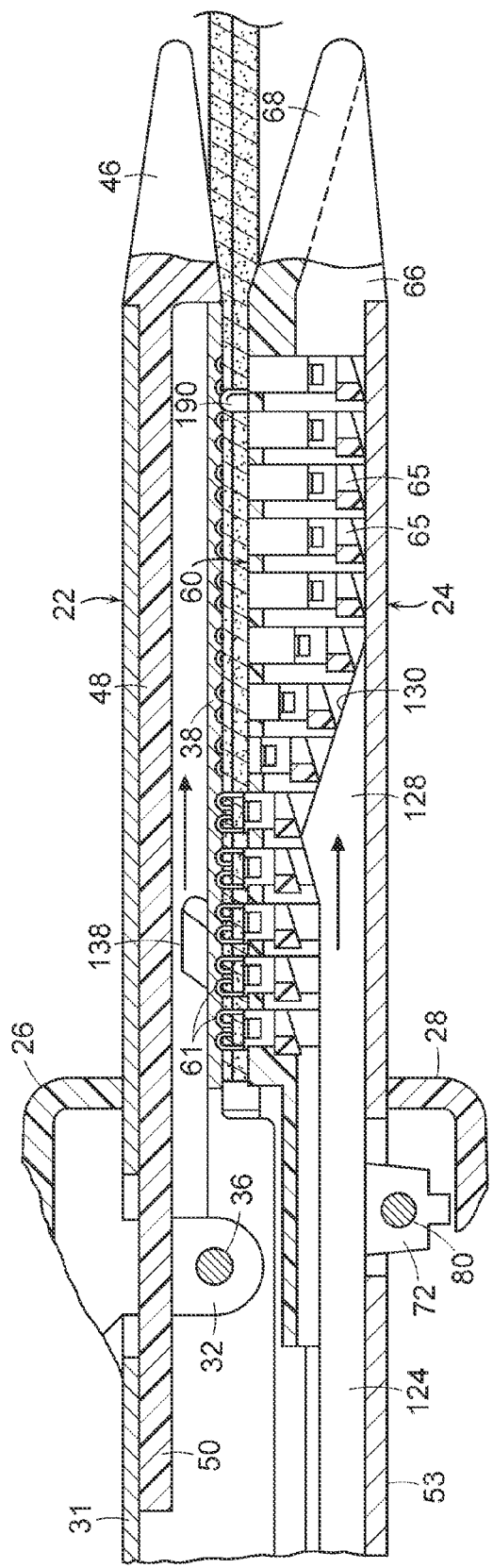
FIG. 17 is a partial cross-sectional view of the anvil and staple cartridge carrying jaw members of FIGS. 5 and 6 illustrating the operation of the pusher bar and knife blade assembly of FIG. 10.

As shown in FIG. 17, a plurality of staple drivers 65 can be slidably mounted in staple openings 64 for actuating the staples 61 which are loaded into staple cartridge 60. Referring to FIG. 6, each staple driver 65 can be designed to simultaneously actuate two staples 61 located in the adjacent rows provided in staple cartridge 60. Thus, in various embodiments, a first set of staple drivers 65 can be provided for actuating the staples 61 in the staggered rows located on one side of central longitudinal slot 62, and a second set of staple drivers 65 can be provided for actuating the staples 61 in the pair of adjacent rows located on the other side of central longitudinal slot 62.

Figure 14:
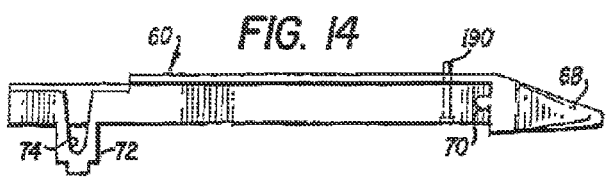
FIG. 14 is a side view of the staple cartridge of the anastomotic stapling instrument of FIG. 1.
Figure 18:
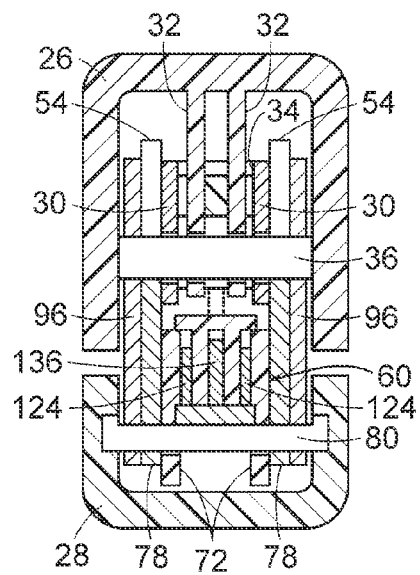
FIG. 18 is a cross-sectional view of the anastomotic stapling instrument of FIG. 1 taken along line 18-18 in FIG. 4.

As shown in FIGS. 2 and 3, similar to the above, the front or distal end of staple cartridge 60 can include a tapered tip 68 to facilitate the insertion of lower jaw member 24 into a hollow, tubular body organ, for example. Immediately behind its tapered tip 68, staple cartridge 60 can be provided with a pair of rearwardly extending protrusions 70 (one shown in FIG. 14) which can be received in corresponding notches provided in side walls 52 of lower jaw member 24. At the rear of staple cartridge 60, a pair of depending arms 72 can extend downwardly from the cartridge. Each arm 72 can be notched to provide a side opening 74. When cartridge 60 is assembled on lower jaw member 24, its protrusions 70 can be received in corresponding notches provided at the front ends of side walls 52 and its depending arms 72 extend downwardly through an opening 76 (FIG. 4) formed in bottom wall 53 of jaw member 24. Lower jaw member 24 can include a pair of depending ears 78 (FIG. 18) extending downwardly from its side walls 52 on opposite sides of opening 76. A pivot pin 80 can extend through holes formed in depending ears 78 of lower jaw member 24 and through side openings 74 of depending arms 72 on staple cartridge 60 to fasten the staple cartridge to the lower jaw member.

Referring to FIG. 2, the stapling instrument 20 can include a latching mechanism, generally 90, for latching upper jaw member 22 and lower jaw member 24 together at an intermediate position along the jaw members. In various embodiments, jaw members 22 and 24 can be latched together at a position adjacent to the proximal ends of anvil 40 and staple cartridge 60. In at least one embodiment, latching mechanism 90 can comprise a latch arm 92 (FIG. 2) pivotally connected to lower jaw member 24 via pivot pin 80 (FIG. 4). Latch arm 92 can be channel-shaped in configuration and can include a pair of opposed, elongated side walls 94 (FIG. 6) which are spaced apart by a distance sufficient to span side walls 52 of lower jaw member 24. Each side wall 94 of latch arm 92 can include an upwardly and forwardly extending hook member 96 provided with a forwardly facing slot 98 for receiving latch pin 36. A shroud 100 can be mounted on the lower surface of latch arm 92. When latch arm 92 is closed, as shown in FIG. 3, shroud 100 can be aligned with the bottom of lower handle 28 to facilitate the handling and operation of stapling instrument 20 by the surgeon. In various embodiments, shroud 100 can be made of plastic or other lightweight materials, for example, while latch arm 92 can be made of stainless steel, for example. As shown in FIG. 7, shroud 100 can include elongated flanges 102 and 104 extending outwardly from its opposite sides which can serve as fingergrips to enable latch arm 92 to be pivoted downwardly from its latched to its unlatched position. When latch arm 92 is moved to its closed or latched position, the surfaces of slots 98 of hook members 96 can cooperate with latch pin 36 which can act as an over-center latch to maintain latch arm 92 in its latched position.

Referring to FIGS. 6 and 10, the preferred embodiment of stapling instrument 20 can include an improved pusher bar and knife blade assembly, generally 110, which can be slidably mounted for longitudinal movement relative to upper and lower jaw members 22 and 24, respectively, for driving staples 61 from staple cartridge 60 into tissue gripped between the jaw members, forming staples 61 against anvil 40, and cutting the tissue along a line between the rows of staples formed in the tissue. Pusher bar and knife blade assembly 110 can include a pusher block 112 (FIG. 6) which can be slidably received within the lower channel-shaped jaw member 24 between its upstanding side flanges 54. As shown in FIG. 11, pusher block 112 can be attached to an actuator knob 114 by a flange 116 which includes a laterally projecting finger 118 provided with a longitudinally extending notch 119 on its top surface. Finger 118 can be snap-fitted into a lateral slot 120 formed in pusher block 112 to locate notch 119 underneath a longitudinal locking bar 121 to secure pusher block 112 and actuator knob 114 together. Flange 116 of actuator knob 114 can extend through and rids along an elongated slot 122 (FIG. 2) formed in one side flange 54 of lower jaw member 24.

Figure 21:
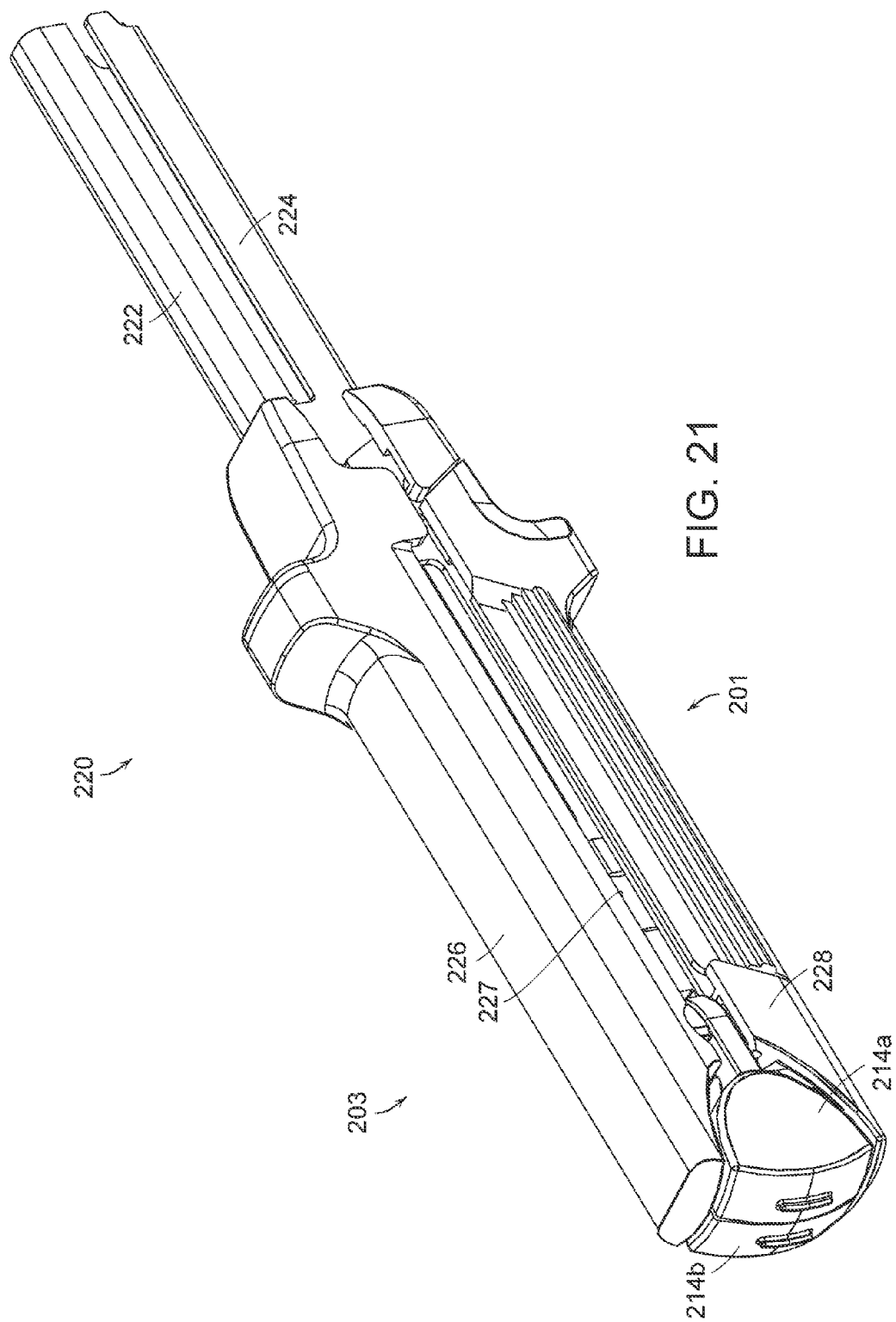
FIG. 21 is a perspective view of a stapling instrument in accordance with one non-limiting embodiment of the present invention.

The pusher bar and knife blade assembly 110 can include a pair of staple pusher bars 124 (FIG. 10) projecting forwardly from pusher block 112 and slidably received in elongated slots 66 (FIG. 16) of staple cartridge 60. Pusher block 112 can be provided with a pair of vertical slots 126 (FIG. 11) in which pusher bars 124 are secured. As shown in FIG. 10, the front end of each staple pusher bar 124 can be provided with a wedge-shaped tip 128 which defines an inclined cam surface 130 for engaging staple drivers 65 as pusher bars 124 are advanced into staple cartridge 60. As shown in FIG. 21, each staple driver 65 can be provided with a sloped surface 132 oriented at the same angle as cam surface 130 of each staple pusher bar 124 to provide a flat, sliding contact between the surfaces.

Referring to FIGS. 6 and 10, the pusher bar and knife blade assembly 110 can include a knife block 134 which is slidably mounted for longitudinal movement along lower jaw member 24 between its upstanding side flanges 54. Knife block 134 can include a knife support bar 136 which extends forwardly into central longitudinal slot 62 of staple cartridge 60. An inclined knife blade 138 provided with a beveled cutting edge 140 can be located at the front end of knife support bar 136. The beveled cutting edge of knife blade 138 can be oriented at an angle relative to elongate jaw members 22 and 24 and can be slidably received in central longitudinal slot 62 of staple cartridge 60.

Figure 19:
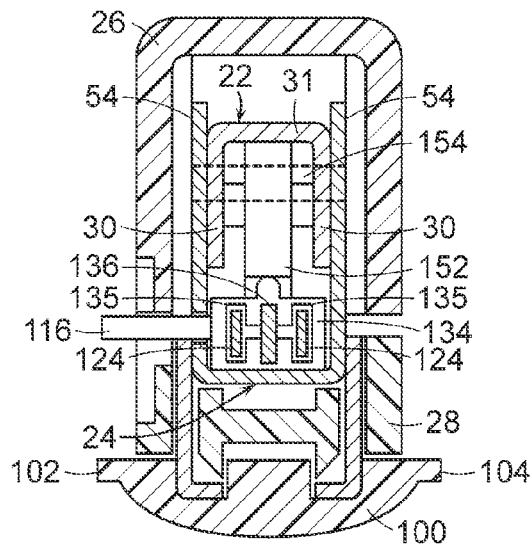
FIG. 19 is a cross-sectional view of the anastomotic stapling instrument of FIG. 1 taken along line 19-19 in FIG. 4.
Figure 20:
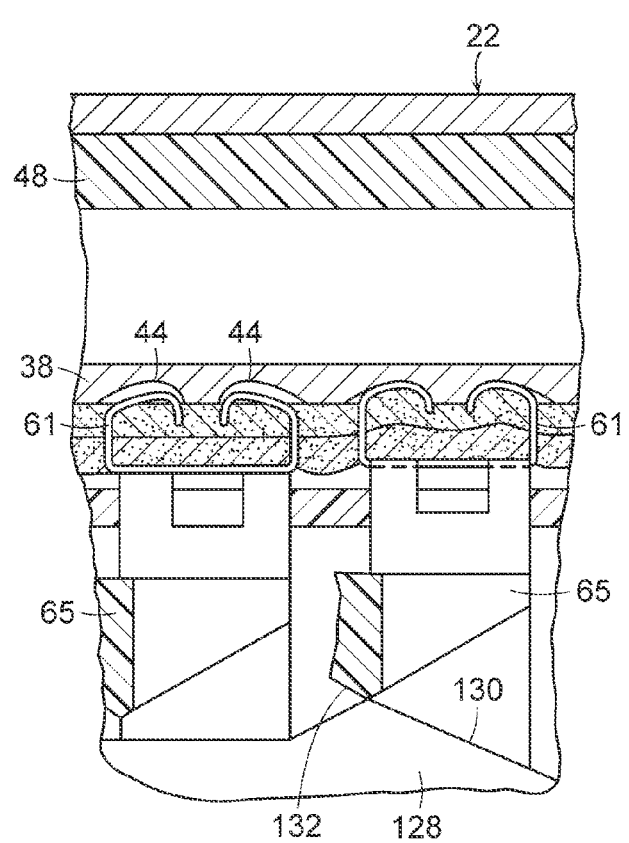
FIG. 20 is a detail view of a portion of the anvil and staple cartridge shown in FIG. 18.

In various embodiments, knife block 134 can include a pair of longitudinal slots 135 (FIG. 19) extending therethrough which slidably receive staple pusher bars 124 to permit pusher block 112 to slide relative to the knife block. Accordingly, when pusher block 112 is advanced toward staple cartridge 60 by actuator knob 114, staple pusher bars 124 can slide through knife block 134 which remains stationary until the pusher block moves into engagement with the knife block. After knife block 134 is engaged by pusher block 112, the knife block and pusher block can advance simultaneously toward staple cartridge 60. As shown in FIG. 17, knife blade 138 can be advanced through staple cartridge 60 along with staple pusher bars 124, forming staples 61 in the tissue gripped between the jaw members and cutting the tissue between the staple rows. Thereafter, when actuator knob 114 is retracted, pusher block 112 can initially slide staple pusher bars 124 backward through knife block 134 which can remain stationary. Each staple pusher bar 124 can include an offset portion 142 which can move into engagement with knife block 134 after staple pusher bars 124 are withdrawn by a predetermined distance. With offset portions 142 of staple pusher bars 124 engaging knife block 134, pusher block 112 and knife block 134 can be simultaneously retracted by actuator knob 114 to return pusher bars 124 and knife blade 138 to the start position.

In accordance with various embodiments of the invention, stapling instrument 20 can be provided with jaw clamping means for applying clamping forces to the jaw members to urge staple cartridge 60 and anvil 40 together during the formation of staples 61. The jaw clamping means can include means for urging the jaw members apart at a position remote from the latching mechanism to resist the forces exerted on staple cartridge 60 and anvil 40 when staples 61 are formed. In at least one embodiment, a cam means can be mounted on one of the jaw members and can be engageable with the other jaw member for moving said jaw members apart at the remote position to urge staple cartridge 60 and anvil 40 together. In various embodiments, a cam member can be pivotally mounted on one of the jaw members at a position remote from the latching mechanism. The cam member can be pivotable from a first inoperative position to a second operative position to move the remote ends of the jaw members apart. The cam member can be operable by pusher block 112 of pusher bar and knife blade assembly 110 to move to its operative position when the pusher block is advanced and to return to its inoperative position when the pusher block is retracted.

In various embodiments, a cam mechanism, generally 150, can be located adjacent to the rear end of lower jaw member 24, as shown in FIG. 4. Cam mechanism 150 can include a cam member 152 pivotally mounted on a transverse pivot pin 154 extending between upstanding side flanges 54 of lower jaw member 24. Cam member 152 can include a first lower cam surface 156 for engaging top wall 31 of upper jaw member 22 with cam 152 in its first inoperative position (FIG. 12) and a second higher cam surface 158 for engaging the top wall 31 of upper jaw member 22 with cam 152 disposed in its second operative position (FIG. 13). First cam surface 156 can be arranged to maintain upper and lower jaw members substantially parallel with cam 152 in its inoperative position. Second cam surface 158 can be arranged to raise the rear end of upper jaw member 22 by approximately 0.125 inch (3.2 mm), for example, when cam 152 pivots from its inoperative position to its operative position. In addition, upper jaw member 22 can be sufficiently flexible to permit the rear portion of upper jaw member 22 to bend upward away from lower jaw member 24 when cam member 152 is moved from its inoperative position to its operative position.

As shown in FIG. 4, cam member 152 can include a radially extending notch 160 which divides the cam into a large front finger 162 and a small rear finger 164. Front cam finger 162 can include a flat, rearwardly facing surface 165, and rear cam finger 164 can include a sloped, forwardly facing surface 166. With cam 152 in its inoperative position, front cam finger 162 and rear cam finger 164 can extend downwardly through an elongated slot 168 formed in bottom wall 53 of lower jaw member 24.

In various embodiments, cam member 152 can be operable by pusher block 112 to move from its inoperative position to its operative position when the pusher block is advanced. As shown in FIG. 11, pusher block 112 can include a pair of rearwardly extending arms 170 which are spaced apart to define a gap 172 therebetween. The rear ends of arms 170 can be connected by a cam actuator pin 174 which extends across gap 172. Referring to FIGS. 4 and 11, with cam member 152 disposed in its inoperative position, front cam finger 162 can extend through gap 172 between arms 170 of pusher block 112, while cam actuator pin 174 can be received in notch 160 between front finger 162 and rear finger 164 of the cam member.

Figure 13:
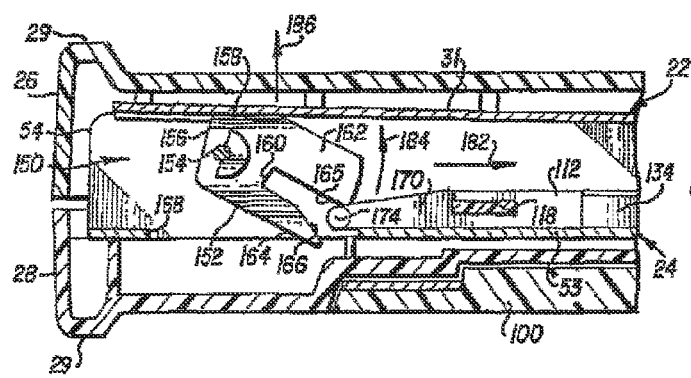
FIG. 13 is a partial cross-sectional view of the rear portion of the anastomotic stapling instrument of FIG. 1 illustrating the cam mechanism in its operative position.

As shown in FIG. 12, with cam member 152 disposed in its first inoperative position, top wall 31 of upper jaw member 22 can rest on first cam surface 156 of the cam member. With cam member 152 in its inoperative position, top wall 31 of upper jaw member 22 can be substantially parallel to bottom wall 53 of lower jaw member 24. In addition, pusher block 112 can be located in its start position spaced rearwardly from knife block 134. When pusher block 112 is advanced, as indicated by arrow 182 (FIG. 13), cam actuator pin 174 can engage rear surface 165 of front cam finger 162 to rotate cam member 152 in a counter-clockwise direction, as indicated by arrow 184, to pivot the cam member to its second operative position and move its second cam surface 158 into engagement with top wall 31 of upper jaw member 22. With cam member 152 pivoted to its operative position, the top wall 31 of upper jaw member 22 can be bent upwardly, as indicated by arrow 186, away from bottom wall 53 of lower jaw member 24. The cam member can apply forces to upper jaw member 22 and lower jaw member 24 which bend the rear portions of the jaw members apart. As a result of the bending the rear portions of upper jaw member 22 and lower jaw member 24 apart, additional clamping forces can be applied to the front portions of upper jaw member 22 and lower jaw member 24 to clamp anvil 40 and staple cartridge 60 against the tissue gripped between the jaw members. Thus, anvil 40 and staple cartridge 60 can be urged together to resist the forces exerted on the anvil and staple cartridge when pusher bar and knife blade assembly 110 is advanced to form staples 61 and cut the tissue.

Referring to FIG. 13, when pusher block 112 is retracted after staples 61 are formed, cam actuator pin 174 can engage sloped surface 166 of rear cam finger 164 to pivot cam member 152 in a clockwise direction. As cam actuator pin 174 moves along sloped surface 166 into notch 160, cam member 152 can pivot in a clockwise direction and return to its first inoperative position (FIG. 12) with its first cam surface 156 in engagement with top wall 31 of upper jaw member 22. As a result, the forces exerted on the rear portions of upper jaw member 22 and lower jaw member 24 by cam 152 can be released and top wall 31 of upper jaw member 22 can return to a substantially parallel relationship with bottom wall 53 of lower jaw member 24. Similarly, the clamping forces applied to the front portions of jaw members 22 and 24 can be released to unclamp anvil 40 and staple cartridge 60.

In various embodiments, stapling instrument 20 can include spacer means mounted on one of the jaw members for maintaining a predetermined gap between staple cartridge 60 and anvil 40 of the stapling instrument. Referring to FIGS. 4 and 6, this spacer means can be embodied as a spacer pin 190 mounted adjacent to the distal end of staple cartridge 60. Spacer pin 190 can extend vertically upward from bottom wall 53 of lower jaw member 24 through staple cartridge 60 and project upwardly from the top of the staple cartridge by a predetermined distance. As shown in FIG. 5, one flange 38 of anvil 40 can include a flange section 192 adjacent to its distal end for engaging spacer pin 190. With the stapling instrument assembled for operation (FIG. 4), spacer pin 190 can engage flange section 192 to maintain a predetermined gap between anvil 40 and staple cartridge 60.

In the operation of stapling instrument 20, the tissue to be stapled and cut can be initially placed between jaw members 22 and 24 and clamped by the jaw members. Thus, handles 26 and 28 can be unlatched by pivotal movement of latch arm 92 downward to its unlatched position (FIG. 2). As a result, the opposite ends of latch pin 36 can be disengaged from slots 98 formed in hook members 96 of latching arm 92. Thereafter, upper and lower jaw members 22 and 24 can be separated by disengaging latch pin 36 from slots 56 formed in side flanges 54 of the lower jaw member.

Next, the tissue to be stapled and cut can be placed on jaw members 22 and 24. For example, as shown in FIG. 17, a piece of tubular, intestinal tissue may be slipped onto the front portion of each jaw member. After the tissue is placed on the jaw member, stapling instrument 20 can be reassembled. The reassembly can be accomplished by aligning latch pin 36 with vertical slots 56 formed in upstanding side flanges 54 of lower jaw member 24. Thereafter, side flanges 54 of lower jaw member 24 can be positioned inside upper handle 26, spanning side walls 30 of upper jaw member 22, while the opposite ends of latch pin 36 can be inserted into vertical slots 56. Finally, latch arm 92 can be pivoted upward to its latched position (FIG. 3) with its cover 100 flush with the bottom of lower handle 28. As a result, hook members 92 can be pivoted over latch pin 36 and slots 98 can receive the opposite ends of the latch pin. Thus, upper jaw member 22 and lower jaw member 24 can be latched together at an intermediate position therealong adjacent to anvil 40 and staple cartridge 60. In addition, spacer pin 190 can engage flange section 192 of anvil 40 through the body tissue to maintain a predetermined gap between anvil 40 and staple cartridge 60.

After the tissue is clamped between the jaw members, stapling instrument 20 can be fired by advancing actuator knob 114 to actuate the pusher bar and knife blade assembly 110. Initially, in the actuation of cam mechanism 150, pusher block 112 and pusher bars 124 (FIG. 4) can be advanced, while knife block 134 can remain stationary. Since only pusher block 112 and its pusher bars 124 are advanced to actuate cam member 152, the initial force required to operate stapling instrument 20 can be minimized.

Referring to FIG. 12, during the initial advance of pusher block 112, pusher bars 124 can slide through knife block 134 and the wedge-shaped tips 128 of the pusher bars can begin to advance through slots 66 of staple cartridge 60. As pusher block 112 advances toward knife block 134, its cam actuator pin 174 can engage rear surface 165 of front cam finger 162 to pivot cam 152 counter-clockwise, as indicated by arrow 184 of FIG. 13, to move the second cam surface 158 of the cam member into engagement with top wall 31 of upper jaw member 22. Cam member 152 can apply forces to upper jaw member 22 and lower jaw member 24 which bend the rear portions of the jaw members apart. As a result, the rear end of top wall 31 of upper jaw member 22 can be bent upward by approximately 0.125 inch (3.2 mm), for example, relative to the rear end of bottom wall 53 of lower jaw member 24. The bending of the rear ends of jaw members 22 and 24 apart can result in additional clamping forces on the front portions of the jaw members to clamp anvil 40 and staple cartridge 60 against the tissue gripped between the jaw members. These additional clamping forces tend to resist the forces exerted on anvil 40 and staple cartridge 60, while the tissue is cut and staples 61 are formed against anvil 40, to maintain the desired spacing between anvil 40 and staple cartridge 60 to produce formed staples 61 which are substantially uniform in height.

Referring to FIG. 13, after cam mechanism 150 is actuated, pusher block 112 can subsequently engage knife block 134 to begin the longitudinal movement of knife block 134 toward staple cartridge 60. In various embodiments, the initial spacing between pusher block 112 and knife block 134 can be arranged such that pusher block 112 engages knife block 134 slightly before cam member 152 arrives at its operative position. Alternatively, the initial spacing between pusher block 112 and knife block 134 can be arranged such that pusher block 112 initially engages knife block 134 after the movement of cam member 152 to its operative position is completed. When pusher block 112 engages knife block 134, the advance of knife blade 138 along central longitudinal slots 42 and 62 of anvil 40 and staple cartridge 60, respectively, can be initiated. Thereafter, staple pusher bars 124 and knife blade 138 can be advanced simultaneously to staple and cut the tissue gripped between anvil 40 and staple cartridge 60.

As pusher block 112 is advanced, staple pusher bars 124 can be moved longitudinally along slots 66 provided in staple cartridge 60. The two wedge-like cam surfaces 130 of staple pusher bars 124 can move through slots 66 into engagement with the sloped surfaces of staple drivers 65 to sequentially drive staples 61 from cartridge 60 and to form staples 61 into B-shaped configuration against anvil flanges 38. The cam surfaces 130 can be located at the same distance from pusher block 112 to simultaneously actuate staple drivers 65 located on opposite sides of central longitudinal slot 62. At the same time, knife block 134 can be advanced to move knife blade 138 through central longitudinal slot 42 of anvil 40 and through central longitudinal slot 62 of staple cartridge 60 to cut the tissue gripped between the jaw members. The additional clamping forces applied to the front portions of upper jaw member 22 and lower jaw member 24 via cam mechanism 150 can tend to resist the forces exerted on anvil 40 and staple cartridge 60 when staples 61 are formed.

After pusher block 112 is fully advanced to form all of the staples in cartridge 60, the pusher block can be retracted toward its start position by retraction of actuator knob 114. Initially, only pusher block 112 can move backward from staple cartridge 60 because staple pusher bars 124 slide through knife block 134 which remains stationary. When offset portions 142 of staple pusher bars 124 engage the front of knife block 134, the knife block can be moved backward from staple cartridge 60 along with pusher block 112. As a result, staple pusher bars 124 and knife blade 138 can be simultaneously retracted from staple cartridge 60 and anvil 40.

As pusher block 112 returns toward its start position, cam actuator pin 174 can engage sloped surface 166 of rear cam finger 164 to pivot cam member 152 in a clockwise direction toward its inoperative position. Cam actuator pin 174 can move along sloped surface 166 into slot 160 between cam fingers 162 and 164 to return cam member 152 to its inoperative position. As a result, second cam surface 158 of cam member 152 can be disengaged from the top wall of upper jaw member 22 and rear end of top wall 31 of upper jaw member 22 and move downwardly into engagement with first cam surface 156. At the same time, front cam finger 162 can pivot downwardly into gap 172 between fingers 170 on pusher block 112, and both cam fingers 162 and 164 can pivot downwardly into slot 168 formed in bottom wall 53 of lower jaw member 24. Thereafter, with cam member 152 in its inoperative position, latching arm 92 can be pivoted downward, as shown in FIG. 2, to permit upper jaw member 22 and lower jaw member 24 to be disassembled. At this point, the cut and stapled tissue can be removed from the jaw members.

As outlined above, a surgical stapling instrument can include an actuator knob, such as actuator knob 114 (FIG. 1), for example, which can be configured to advance a pusher bar assembly, such as pusher bar assembly 110 (FIG. 10), within a staple cartridge of the surgical stapling instrument. In various embodiments, actuator knob 114 can be configured to be grasped by a surgeon such that the surgeon can apply a force thereto. In various circumstances, actuator knob 114 can come into contact with or abut tissue surrounding the surgical site when it is advanced distally. In at least one circumstance, as a result, the surgeon may have to reposition the stapling instrument such that actuator knob 114 can pass by the tissue. In other circumstances, the surgeon may have to force actuator knob 114 by the tissue. In either event, such circumstances may be unsuitable and, as a result, there exists a need for a stapling instrument having an actuator knob which can be manipulated to reduce the possibility that the actuator knob may impinge on the surrounding tissue.

Figure 22:
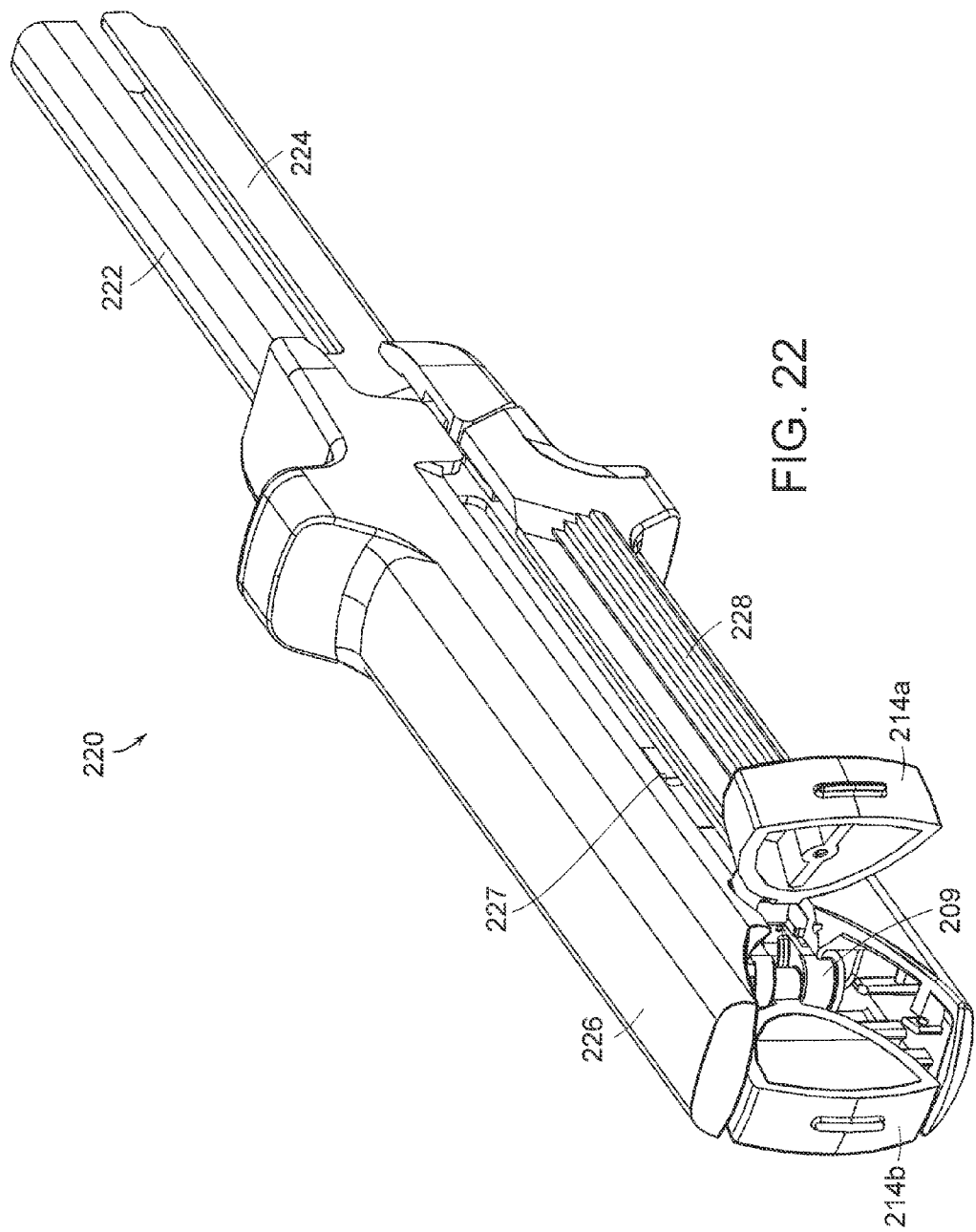
FIG. 22 is a perspective view of the stapling instrument of FIG. 21 illustrating a first actuator knob in an extended position.
Figure 24:
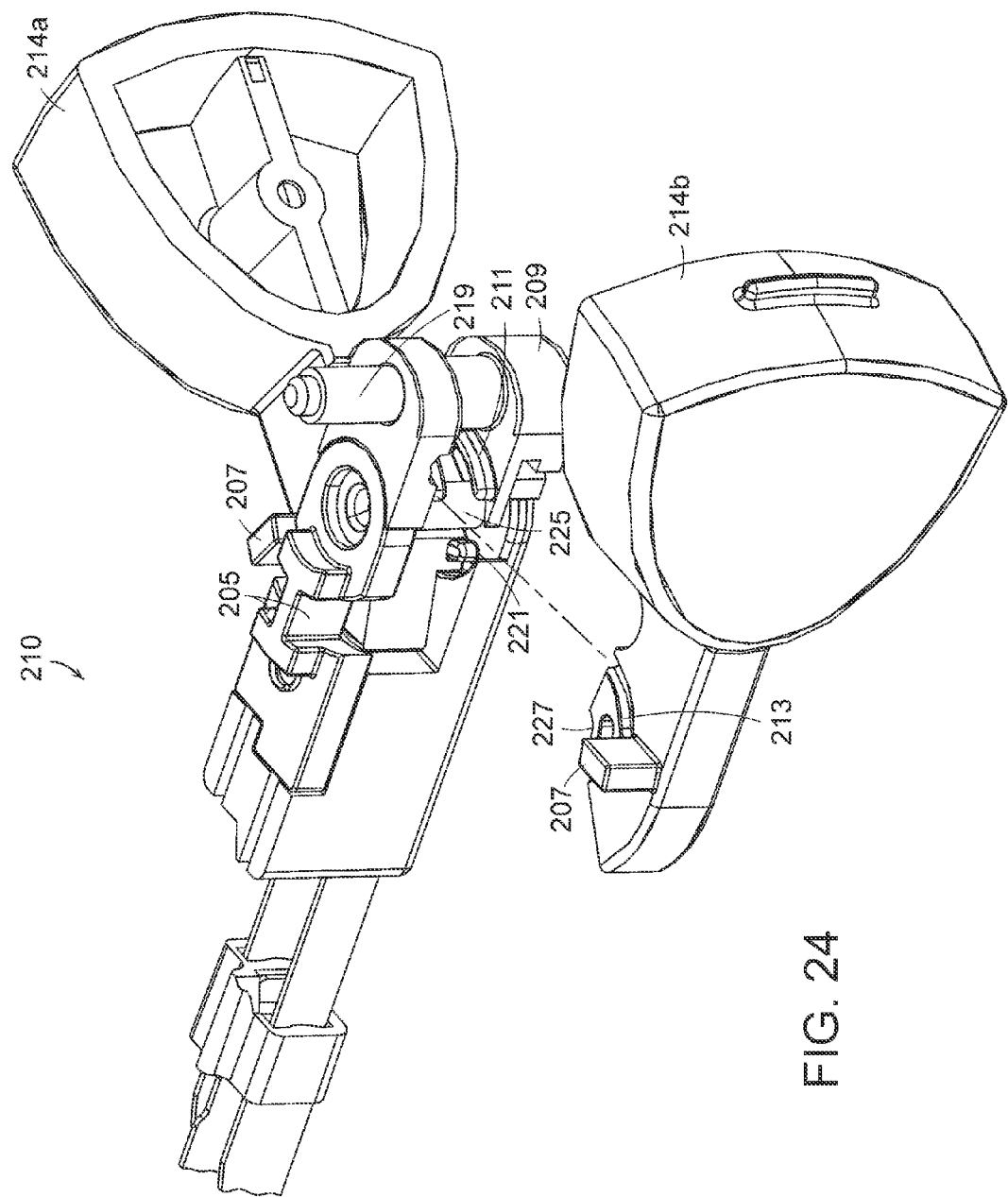
FIG. 24 is an exploded view of a clutch mechanism for operably engaging one or more actuator knobs with a pusher bar of the stapling instrument of FIG. 21.

In various embodiments of the present invention, referring to FIG. 21, stapling instrument 220 can include anvil carrying jaw member 222 extending from upper handle 226, staple cartridge carrying jaw member 224 extending from lower handle 228, and actuator knobs 214a and 214b which can be operably engaged with a pusher bar assembly, such as pusher bar assembly 210 as illustrated in FIG. 24, for example. In various embodiments, a staple cartridge can be removably attached to staple cartridge carrying jaw member 224, for example, such that, after the staple cartridge has been expended, it can be replaced with another staple cartridge. In at least one embodiment, pusher bar assembly 210 can include a staple driver integrally-formed with or operably mounted thereto which can be moved through the staple cartridge as outlined above. In at least one other embodiment, the staple cartridge can include a staple driver contained therein which can be engaged with and pushed distally by the pusher bar assembly. In any event, first actuator knob 214a, for example, can be rotated between a first position (FIG. 21) in which it is operably disengaged from pusher bar assembly 210 and a second position (FIG. 22) in which it is operably engaged with pusher bar assembly 210. Similarly, second actuator knob 214b can be configured to be rotated between first and second positions in which it is operably disengaged and engaged, respectively, with pusher bar assembly 210.

Figure 23:
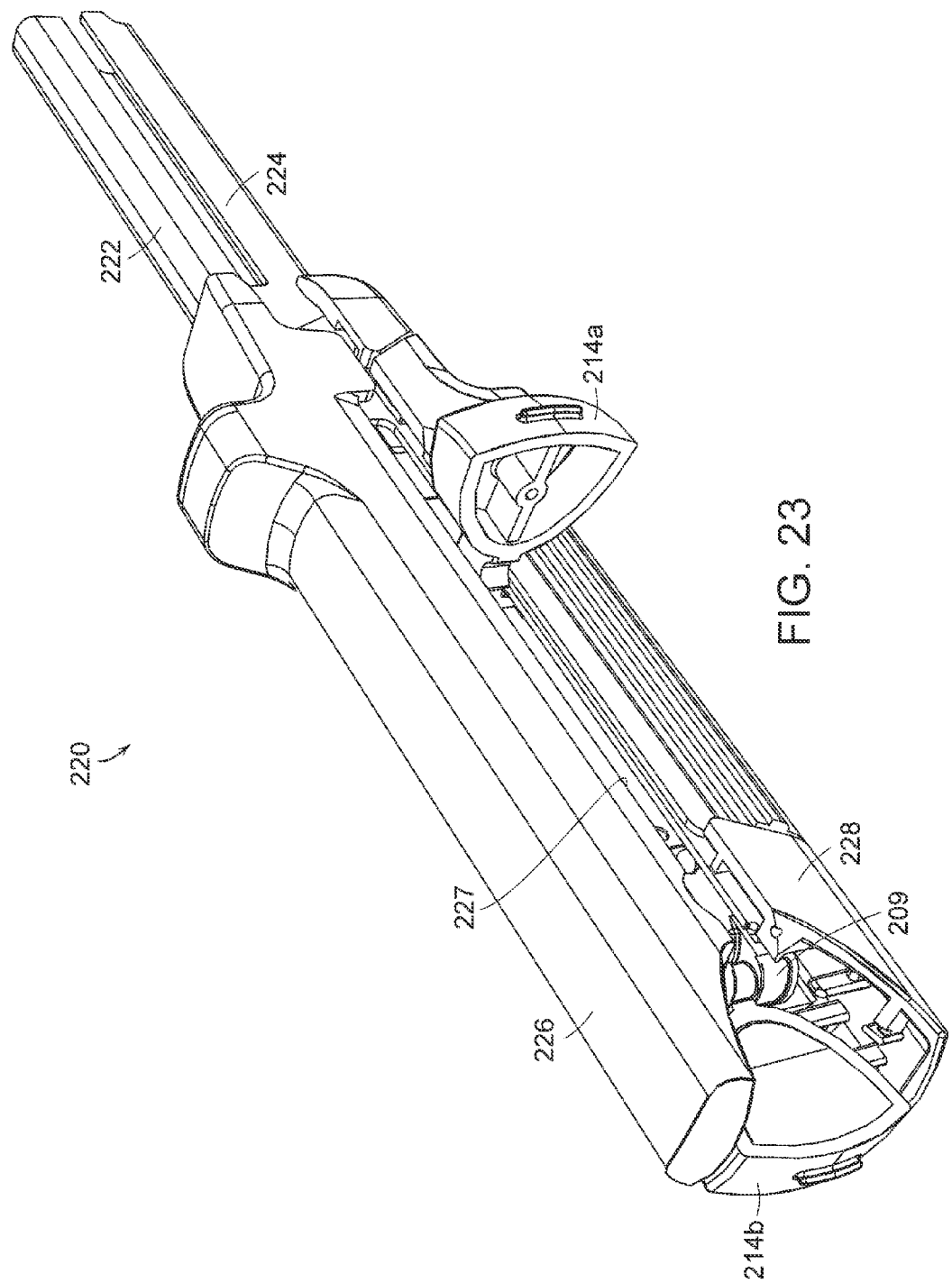
FIG. 23 is a perspective view of the stapling instrument of FIG. 21 illustrating the extended actuator knob of FIG. 22 after it has been advanced distally.
Figure 28:
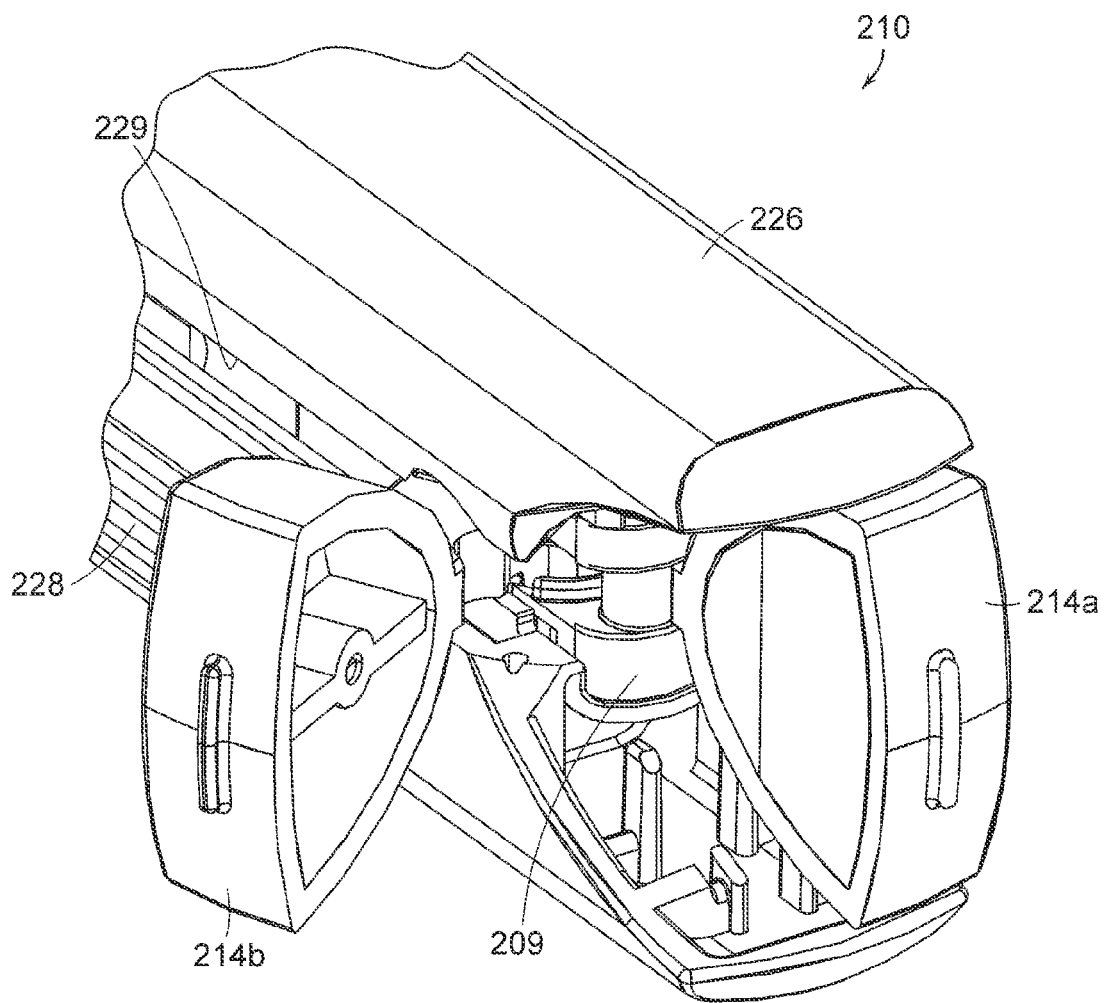
FIG. 28 is a perspective view of the stapling instrument of FIG. 21 illustrating the first actuator knob in a retracted position and a second actuator knob in an extended position.

In various embodiments, as a result of the above, the actuator knobs of a stapling instrument can be selectively engaged with a pusher bar assembly such that, in the event that an actuator knob may come into contact with or abut tissue surrounding the surgical site when it is advanced, that actuator knob can remain in its retracted position while another actuator knob can be extended to advance the pusher bar assembly distally. In at least one such embodiment, referring to FIG. 22, first actuator knob 214a can be rotated into its second position such that it can be operably engaged with pusher bar assembly 210 while second actuator knob 214b can remain in its retracted position. Thereafter, referring to FIG. 23, first actuator knob 214a can be advanced distally relative to upper handle 226 and lower handle 228 along first side 201 of surgical stapler 210 in order to motivate pusher assembly 210. In at least one embodiment, first actuator knob 214a can be slid within first slot 227 defined between, or within, upper handle 226 and lower handle 228. In various other circumstances, referring to FIG. 28, first actuator knob 214a can remain in its retracted position while second actuator knob 214b can be rotated into its extended position. Similar to the above, second actuator knob 214b can be advanced distally along second side 203 of stapling instrument 210 to advance pusher bar assembly 210 within second slot 229, for example. In at least one embodiment, both actuator knobs 214 can be extended to advance pusher bar assembly 210 distally. In various alternative embodiments, although not illustrated, a stapling instrument can include more than two actuator knobs which can be selectively utilized to motivate a pusher bar and/or knife blade assembly. In effect, as a result of the above, the actuator knobs of a surgical instrument can be engaged with a pusher bar assembly independently of each other.

Figure 25:
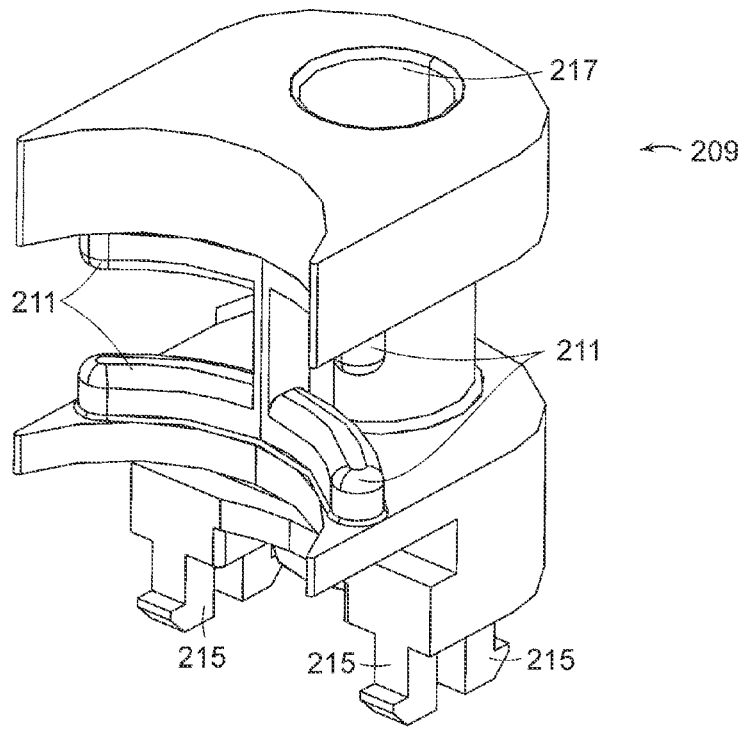
FIG. 25 is a perspective view of a guide member of the clutch mechanism of FIG. 24.
Figure 26:
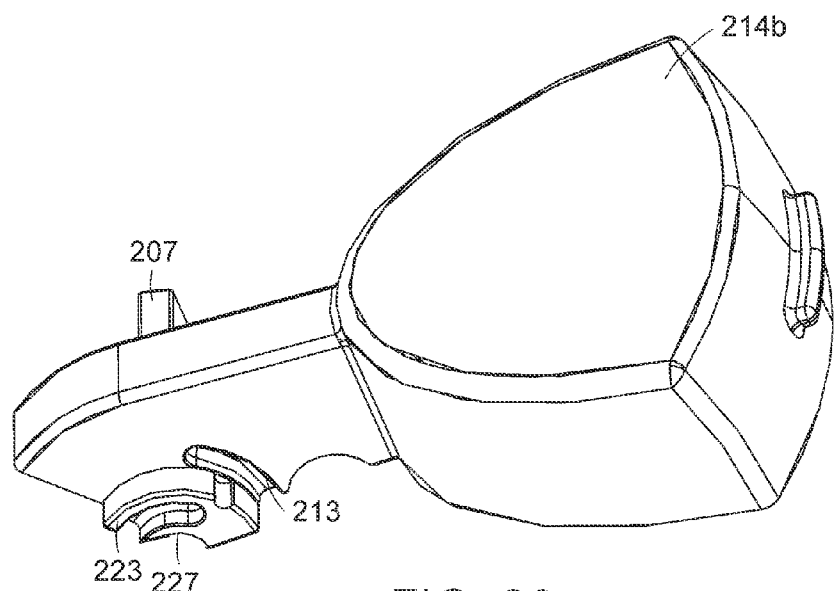
FIG. 26 is a perspective view of an actuator knob of the stapling instrument of FIG. 21.
Figure 27:
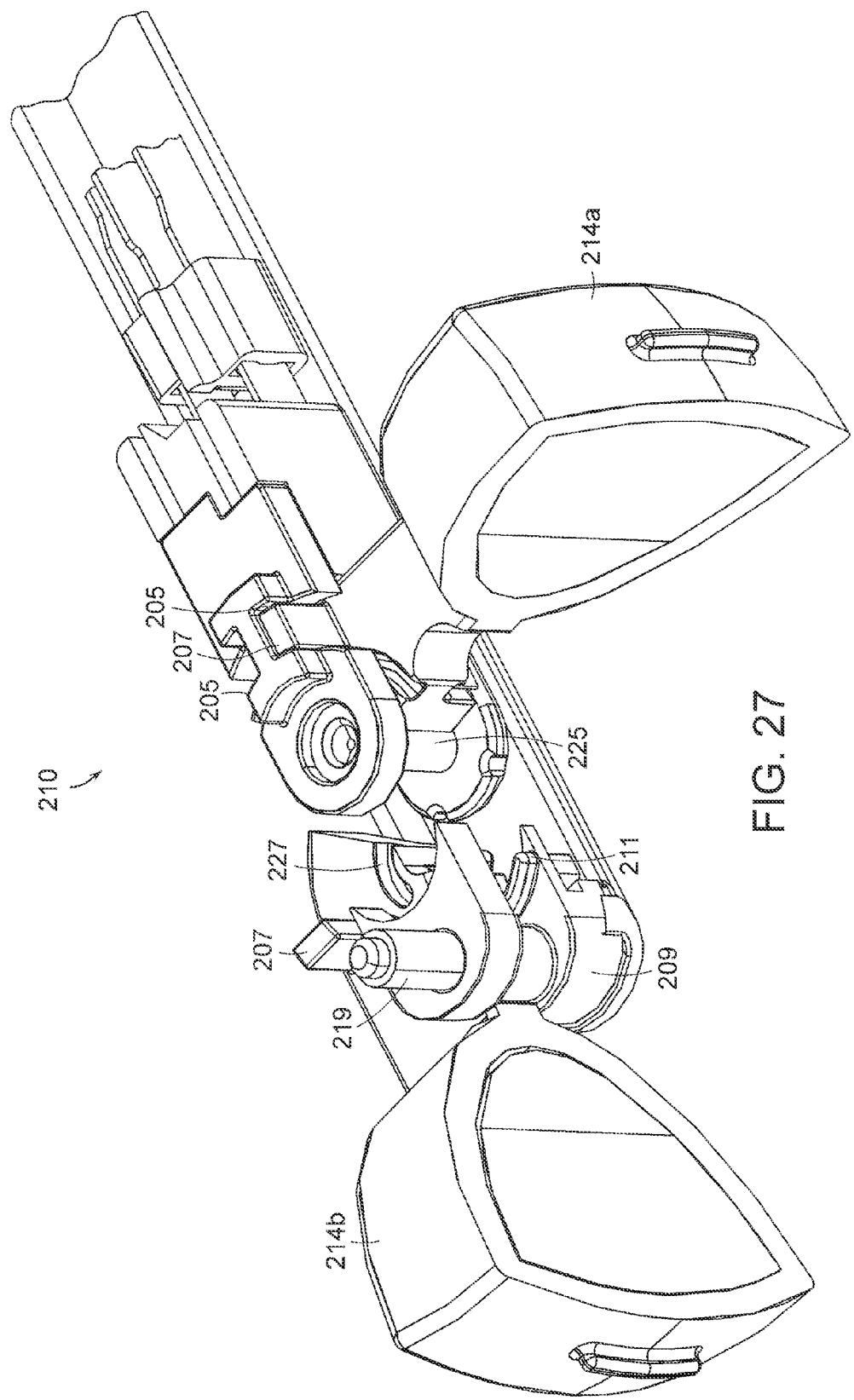
FIG. 27 is another perspective view of the clutch mechanism of FIG. 24.

In various embodiments, further to the above, the actuator knobs of a stapling instrument can be situated in a first position in which they can be held in position and held out of operative engagement with a pusher bar assembly. In at least one embodiment, referring to FIG. 24, stapling instrument 201 can further include guide member 209 which can be configured to guide actuator knobs 214 as they are rotated between their first and second positions. In various embodiments, referring to FIGS. 24-26, guide member 209 can include guide rails 211 which can be slidably received within grooves 213 of actuator knobs 214 such that, when actuator knobs 214 are rotated, guide member 209 can dictate the path along which the actuator knobs 214 are moved. Furthermore, guide rails 211 and grooves 213 can comprise interlocking features which can cooperatively prevent actuator knobs 214 from being unintentionally displaced proximally and/or distally, for example. In at least one such embodiment, guide member 209 can prevent one or more of actuator knobs 214 from being translated along with pusher bar assembly 210 when pusher bar assembly 210 is advanced distally as described above. In various embodiments, a slight friction or interference fit can be present between guide rails 211 and grooves 213 such that the possibility that actuator knobs 214 may be unintentionally rotated into their extended positions can be reduced. Although not illustrated, the actuator knobs can include guide rails extending therefrom which can be slidably received in grooves within the guide member, for example. In any event, referring to FIG. 25, guide member 209 can include one or more retention members 215 which can be configured to retain guide member 209 in position intermediate upper handle 226 and lower handle 228. Furthermore, referring to FIGS. 24 and 25, guide member 209 can include aperture 217 which can be configured to receive retention pin 219 extending therethrough wherein retention pin 219 can be configured to be engaged with upper handle 226 and/or lower handle 228 to retain guide member 209 in position.

In various embodiments, as actuator knobs 214 are rotated between their first and second positions as described above, grooves 213 can be rotated out of engagement with guide rails 211 and actuator knobs 214 can be operatively engaged with pusher bar assembly 210. In at least one embodiment, referring primarily to FIG. 24, pusher bar assembly 210 can include a first clutch feature, such as slots or grooves 205, for example, and actuator knobs 214 can each include a second clutch feature, such as projections 207, for example, wherein the first and second clutch features can be operatively engaged with each other in order to operatively engage one or more of actuator knobs 214 with pusher bar assembly 210. In at least one such embodiment, projections 207 can be closely received within slots 205 such that, when a force is applied to one or more of actuator knobs 214, the force can be transmitted to pusher bar assembly 210 through projections 207 and the sidewalls of slots 205. In at least one embodiment, similar to the above, a slight friction or interference fit can be present between projections 207 and slots 205 to hold actuators 214 in their extended position. In any event, although not illustrated, the first clutch feature can include projections extending from the pusher bar assembly which can be configured to be received within recesses or slots within the actuator knobs. In addition to or in lieu of the above, referring to FIG. 24, pusher bar assembly 210 can further include second guide rails 221 which can be configured to be slidably received within slots or grooves 223 within actuator knobs 214, wherein rails 221 and grooves 223 can be configured to guide actuator knobs 214 into their second position and/or transmit forces from actuator knobs 214 to pusher bar assembly 210 once they are in their second position. Similar to guide rails 211, guide rails 221 can be configured to create a slight friction or interference fit with grooves 223 to hold actuator knobs 214 in position. Further to the above, in various embodiments, actuator bar 210 can include post 225 about which actuator knobs 214 can be rotated. In at least one embodiment, actuator knobs 214 can include recesses 227 which can be contoured such that the sidewalls of recesses 227 can closely receive and slide around post 225 and, as a result, post 225 can guide actuator knobs 214 as they are rotated between their first and second positions, for example.

Figure 30:
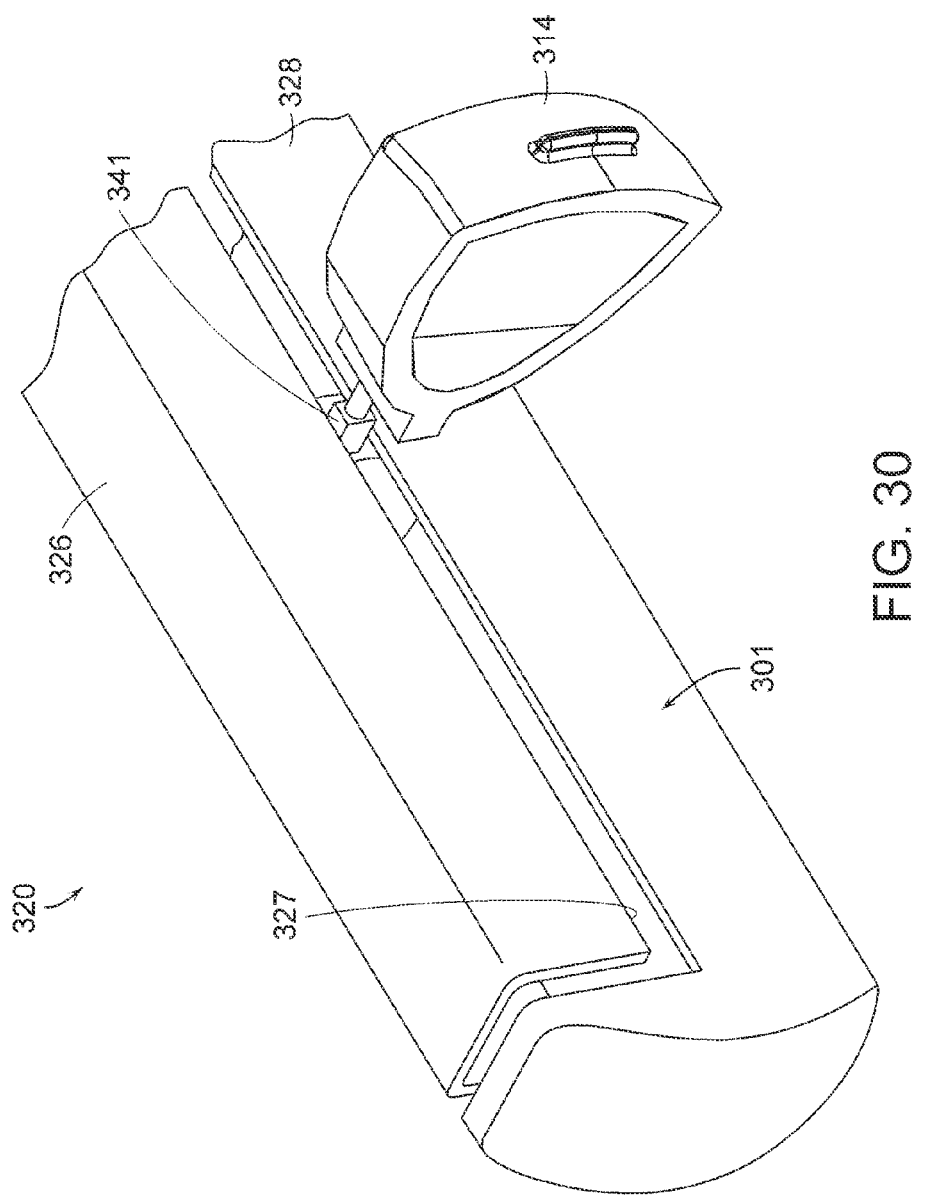
FIG. 30 is a partial perspective view of the stapling instrument of FIG. 29 illustrating an actuator knob after it has been advanced distally along a first side of the stapling instrument.
Figure 31:
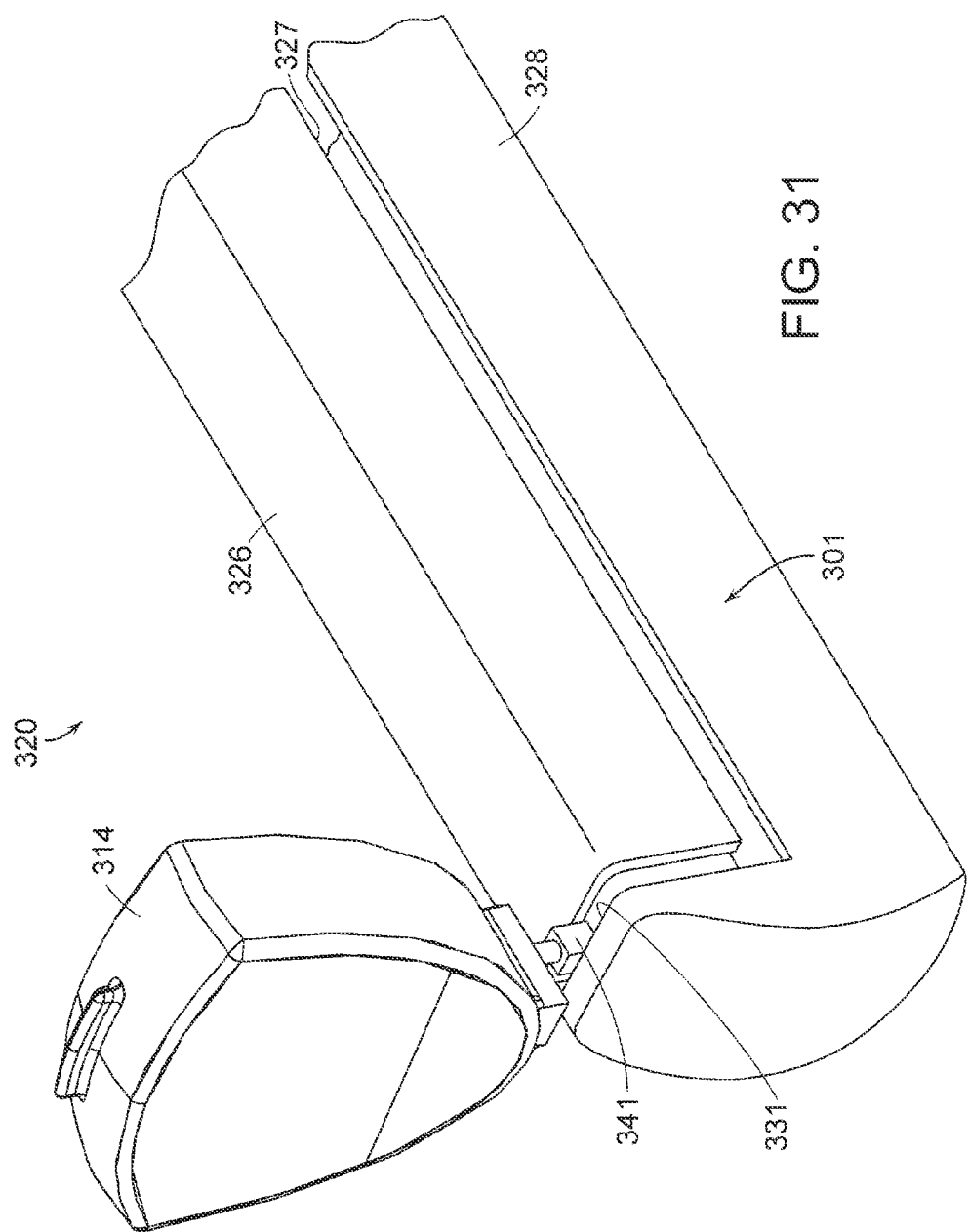
FIG. 31 is a partial perspective view of the stapling instrument of FIG. 29 illustrating the actuator knob of FIG. 30 being rotated between a first position and a second position.
Figure 32:
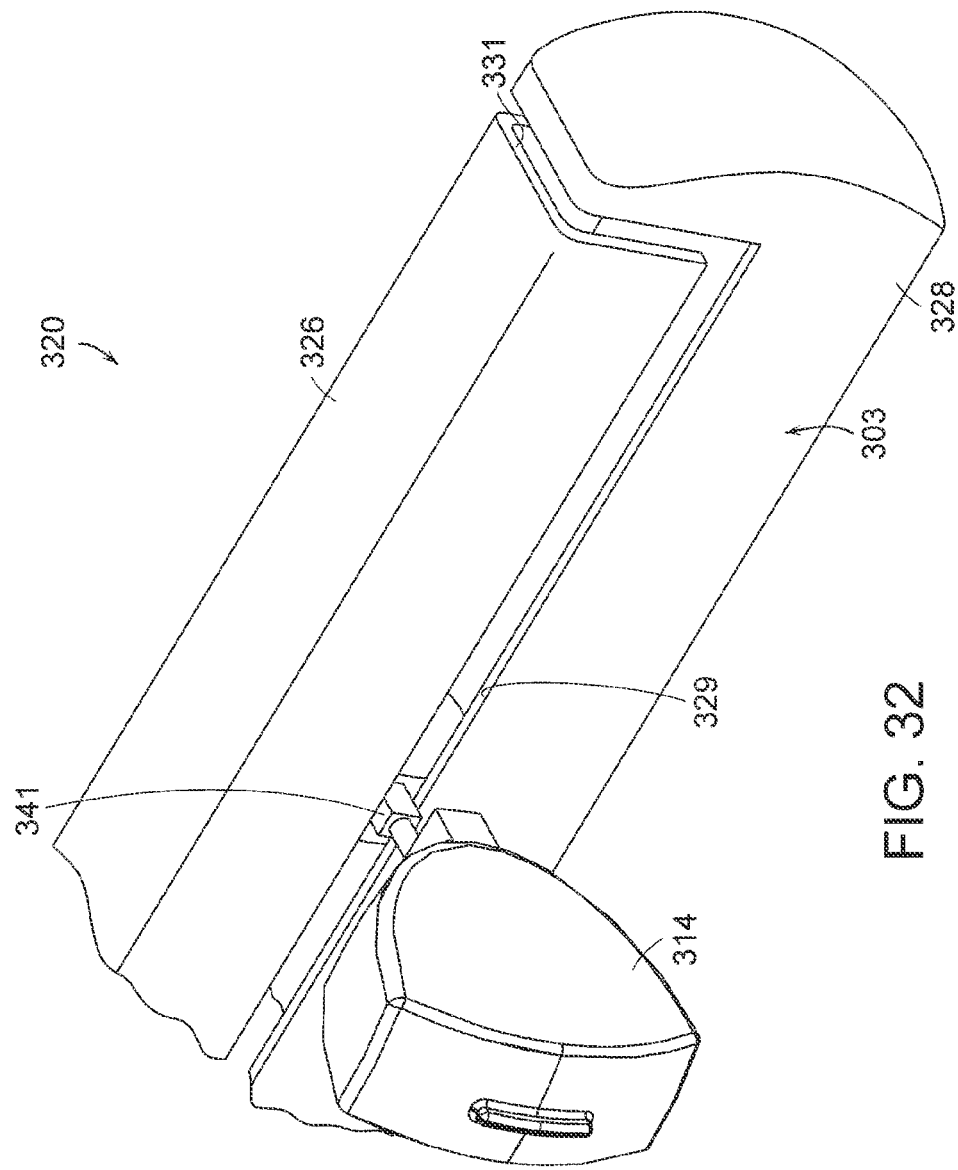
FIG. 32 is a partial perspective view of the stapling instrument of FIG. 29 illustrating the actuator knob of FIG. 30 after it has been advanced distally along a second side of the stapling instrument.

In various embodiments of the present invention, a stapling instrument can include an actuator knob which can be configured to be selectively advanced along a first side of the stapling instrument and a second side of the stapling instrument. In at least one embodiment, referring to FIGS. 29 and 30, stapling instrument 320 can include an upper handle 326, a lower handle 328, and an actuator knob 314, wherein actuator knob 314 can, similar to the above, be configured to advance a pusher bar assembly within a staple cartridge. In at least one embodiment, upper handle 326 and lower handle 328 can define first slot 327 and second slot 329 therebetween, wherein slots 327 and 329 can both be configured to permit actuator knob 314 to slide therethrough. More particularly, in various embodiments, actuator knob 314 can be configured such that it can be selectively slid through first slot 327 along first side 301 or, alternatively, through second slot 329 along second side 303. In various embodiments, referring to FIG. 31, stapling instrument 320 can further include third slot 331 which can be configured to allow actuator knob 314 to be moved from one side of the stapling instrument to the other. In at least one such embodiment, as a result, a surgeon can selectively position actuator knob 314 such that, if it appears that actuator knob 314 may impinge on tissue if it is advanced distally on one side of the stapling instrument, actuator knob 314 can rotated over to the other side of the stapling instrument before it is advanced. Although the first and second sides of the illustrated embodiment are located on opposite sides of surgical instrument 320, other embodiments are envisioned where the first and second slots, for example, are located on adjacent sides and/or sides which are not directly opposite to each other. Furthermore, other embodiments are envisioned in which the sides of a stapling instrument are not readily discernable, such as instruments having round and/or arcuate portions.

Figure 29:
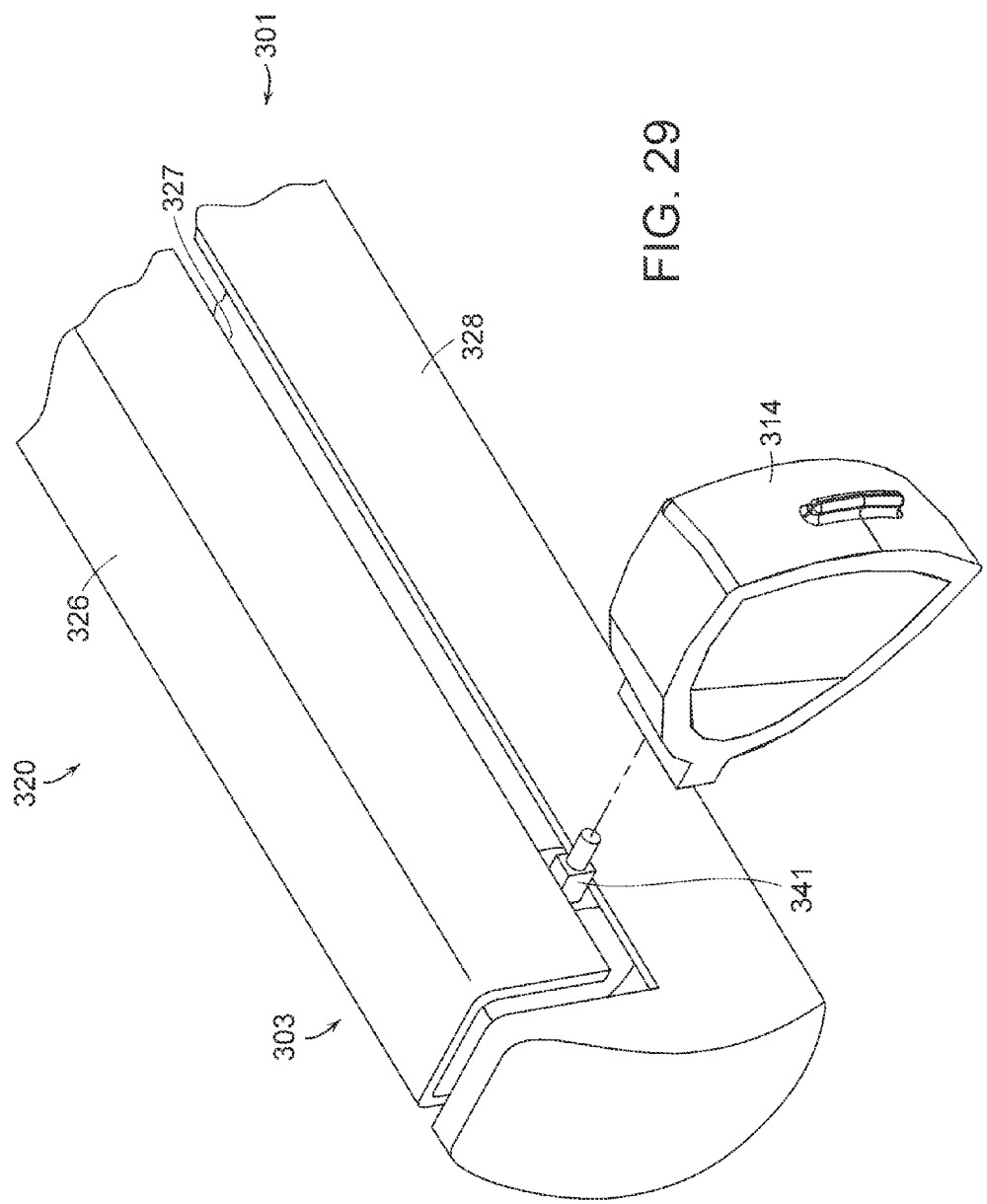
FIG. 29 is a partial exploded view of a stapling instrument in accordance with one non-limiting embodiment of the present invention.

In various embodiments, referring primarily to FIG. 29, first slot 327 can be configured such that it defines a path for actuator knob 314 which is parallel to, or at least substantially parallel to, a path defined by second slot 329. In at least one embodiment, third slot 331 can be configured to connect first slot 327 and second slot 329 such that it can define a path for actuator knob 314 which is perpendicular to, or at least substantially perpendicular to, the paths defined by slots 327 and 329. In such embodiments, actuator knob 314 can be rotated over the top of the surgical instrument to move actuator knob 314 from first side 301 to second side 303. In the event that a surgeon decides to reposition actuator knob on first side 301, the surgeon can move actuator knob 314 back through slot 311 until it is positioned within first slot 327 once again. In various alternative embodiments, although not illustrated, a third slot can define a path for actuator knob 314 which is parallel to, or at least substantially parallel to, and/or co-planar with, or at least substantially co-planar with, the paths defined by slots 327 and 329. In further various embodiments, a third slot can define a path which is skew with respect to the paths defined by slots 327 and 329. In any event, a third slot can be configured connect first and second slots such that an actuator knob can be slid therewithin.

Figure 33:
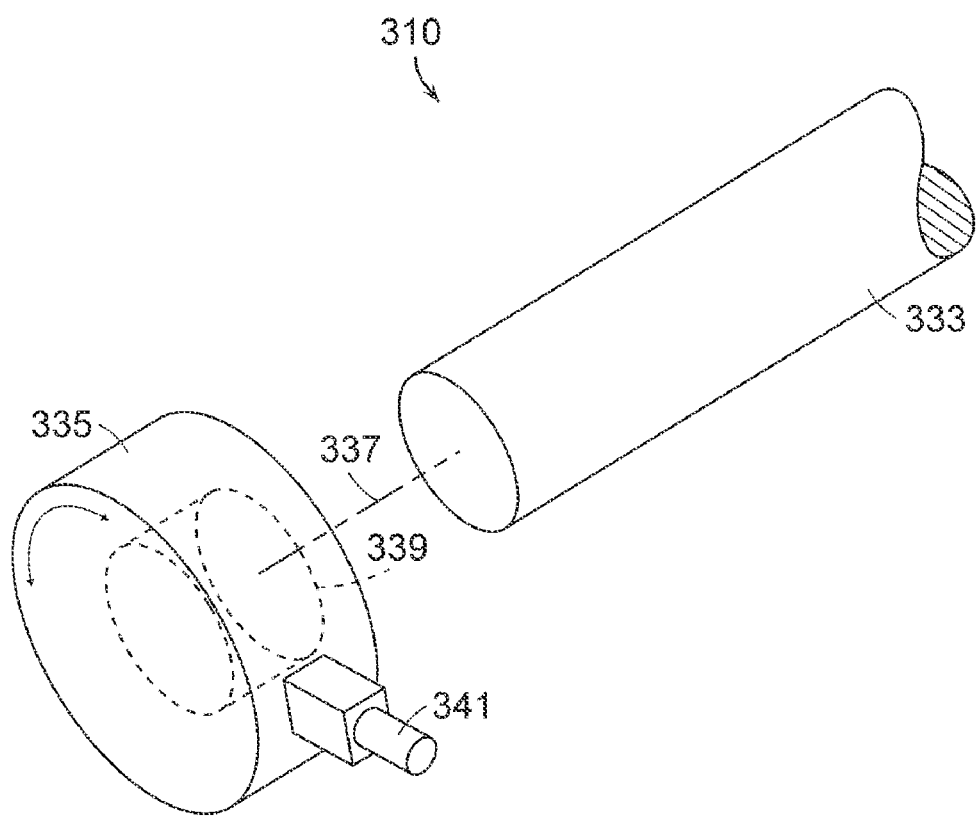
FIG. 33 is an exploded view of a pusher bar assembly of the stapling instrument of FIG. 29 configured to allow the actuator knob of FIG. 30 to be rotated between its first and second positions.

As outlined above, stapling instrument 320 can include a pusher bar assembly which can be operably engaged with actuator knob 314, for example, such that actuator knob 314 can be configured to advance the pusher bar assembly distally. In various embodiments, referring to FIG. 33, stapling instrument 320 can include pusher bar assembly 310 which can include a first portion 333 operably engaged with a knife assembly, for example, and, in addition, a second portion 335 which can be rotatably mounted to first portion 333. In at least one embodiment, first portion 333 can define an axis 337 about which second portion 335 can be rotated. In at least one such embodiment, second portion 335 can include aperture 339 defined therein which can be configured to closely receive first portion 333. In at least one embodiment, although not illustrated, pusher bar assembly 310 can further include one or more retaining members, such as set screws, for example, configured to extend into a groove in first portion 333, for example, for retaining second portion 335 to first portion 333. In various embodiments, second portion 335 can include mount 341 extending therefrom which can be configured to retain actuator knob 314 to second portion 335. In order to move actuator knob from a first side of stapling instrument 320 to the another side, as described above, actuator knob 314 and second portion 335 can be rotated relative to first portion 333 such that actuator knob 314 can be selectively positioned within first slot 327 and second slot 329. In at least one embodiment, although not illustrated, a stapling instrument can have more than two slots for receiving an actuator knob when it is advanced within a staple cartridge. In any event, in various alternative embodiments, first portion 333 and second portion 335 can be fixedly mounted together such that they are rotated together about axis 337. In at least one such embodiment, first portion 333 can be configured to rotate relative to a substantially non-rotatable portion of pusher bar assembly 310.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical stapling instrument, comprising:
    a housing having a first side and a second side;
    a first jaw member configured to operably support a staple cartridge having at least two rows of staples stored therein, wherein at least one of said first jaw member and the staple cartridge is configured to slidably support a staple driver configured to deploy the staples from the staple cartridge;
    a second jaw member configured to operably support an anvil configured to deform the staples when the staples are deployed from the staple cartridge;
    a pusher bar configured to move the staple driver relative to said first jaw member and said second jaw member; and
    an actuator knob configured to receive a force thereto, wherein said actuator knob is rotatably mounted to said pusher bar, wherein said actuator knob is configured to be rotated between a first position and a second position, wherein said actuator knob is configured to be moved along said first side when said actuator knob, is in said first position, and wherein said actuator knob is configured to be moved along said second side when said actuator knob is in said second position,
    wherein said housing further comprises:
        a first slot defined within said first side, wherein said actuator knob is configured to slide within said first slot when said actuator knob is in said first position;
        a second slot defined within said second side, wherein said actuator knob is configured to slide within said second slot when said actuator knob is in said second position; and
        a third slot connecting said first slot and said second slot, wherein said actuator knob is configured to slide within said third slot to selectively move said actuator knob between said first position and said second position.

2. The surgical stapling instrument of claim 1, wherein said third slot is substantially co-planar with said first slot and said second slot.

3. The surgical stapling instrument of claim 1, wherein said third slot is one of perpendicular to and transverse to said first slot and said second slot.

4. The surgical stapling instrument of claim 1, wherein said first slot is substantially parallel to said second slot.

5. The surgical stapling instrument of claim 1, wherein said pusher bar defines an elongate axis, and wherein said actuator knob is rotatable about said axis.

6. The surgical stapling instrument of claim 1, wherein said first side is substantially parallel to said second side.

7. The surgical stapling instrument of claim 1, further comprising:
    said anvil;
    said staple cartridge;
    said staple driver; and
    a cutting member operably engaged with said staple driver.

8. A surgical stapling instrument, comprising:
    a housing having a first slot and a second slot;
    a first jaw member configured to operably support a staple cartridge having at least two rows of staples stored therein, wherein at least one of said first jaw member and the staple cartridge is configured to slidably support a staple driver configured to deploy the staples from the staple cartridge, and wherein said first law member includes a distal end;
    a second jaw member configured to operably support an anvil configured to deform the staples when the staples are deployed from the staple cartridge, wherein said second jaw member includes a distal end;
    a pusher bar configured to move the staple driver relative to said first jaw member and said second jaw member; and
    an actuator knob extending from said pusher bar, wherein said actuator knob is configured to be selectively positioned within one of said first slot and said second slot and moved toward said distal ends of said first and second jaw members,
    wherein said housing further comprises a third slot connecting said first slot and said second slot, and wherein said actuator knob is configured to slide within said third slot to be selectively positioned within said first slot and said second slot.

9. The surgical stapling instrument of claim 8, wherein said third slot is substantially co-planar with said first slot and said second slot.

10. The surgical stapling instrument of claim 8, wherein said third slot is one of perpendicular to and transverse to said first slot and said second slot.

11. The surgical stapling instrument of claim 8;
wherein said first slot is substantially parallel to said second slot.

12. A surgical stapling instrument, comprising:
a housing;
a first jaw member configured to operably support a staple cartridge having at least two rows of staples stored therein, wherein at least one of said first jaw member and the staple cartridge is configured to slidably support a staple driver configured to deploy the staples from the staple cartridge;
a second jaw member configured to operably support an anvil configured to deform the staples when the staples are deployed from the staple cartridge;
a pusher bar configured to move the staple driver relative to said first jaw member and said second jaw member; and
a first actuator knob selectively engageable with said pusher bar, wherein said first actuator knob is rotatable between a first position and a second position, wherein said first actuator knob is operably disengaged from said pusher bar when it is in said first position, and wherein said first actuator knob is operably engaged with said pusher bar when it is in said second position;
a second actuator knob selectively engageable with said pusher bar independently of the selective engagement of said first actuator knob with said pusher bar, wherein said second actuator knob is rotatable between a third position and a fourth position, wherein said second actuator knob is operably disengaged from said pusher bar when it is in said third position, wherein said second actuator knob is operably engaged with said pusher bar when it is in said fourth position, and wherein said first actuator knob can be rotated between said first position and said second position independently of said second actuator knob being rotated between said third position and said fourth position;
a first slot defined within said housing, wherein said first actuator knob is configured to slide within said first slot to move said pusher bar toward said first and second jaw members; and
a second slot defined within said housing, wherein said second actuator knob is configured to slide within said second slot to move said pusher bar toward said first and second jaw members.

13. The surgical stapling instrument of claim 12, wherein said pusher bar includes a first clutch feature, and wherein said first actuator knob includes a second clutch feature configured to engage said first clutch feature to operably engage said first actuator knob with said pusher bar when said first actuator knob is in said second position.

14. The surgical stapling instrument of claim 13, wherein said first clutch feature includes a groove and said second clutch feature includes a projection configured to be received within said groove.

15. A surgical stapling instrument, comprising:
a housing comprising a first side and a second side;
a member configured to operably support a staple cartridge comprising staples stored therein, wherein at least one of said member and the staple cartridge is configured to slidably support a staple driver configured to deploy the staples from the staple cartridge;
a drive bar configured to move the staple driver relative to said member; and
an actuator configured to receive a force thereto, wherein said actuator is rotatably mounted to said drive bar, wherein said actuator is configured to be rotated between a first position and a second position, wherein said actuator is configured to be moved along said first side when said actuator is in said first position, and wherein said actuator is configured to be moved along said second side when said actuator is in said second position,
wherein said housing further comprises:
a first slot defined within said first side, wherein said actuator is configured to slide within said first slot when said actuator is in said first position;
a second slot defined within said second side, wherein said actuator is configured to slide within said second slot when said actuator is in said second position; and
a third slot connecting said first slot and said second slot, wherein said actuator is configured to slide within said third slot to selectively move said actuator between said first position and said second position.

16. The surgical stapling instrument of claim 15, wherein said third slot is substantially co-planar with said first slot and said second slot.

17. The surgical stapling instrument of claim 15, wherein said third slot is one of perpendicular to and transverse to said first slot and said second slot.

18. A surgical stapling instrument, comprising:
a housing having a first slot and a second slot;
a member configured to operably support a staple cartridge comprising staples stored therein, wherein at least one of said member and the staple cartridge is configured to slidably support a staple driver configured to deploy the staples from the staple cartridge, and wherein said member comprises a distal end;
a drive bar configured to move the staple driver relative to said member; and
an actuator extending from said drive bar, wherein said actuator is configured to be selectively positioned within one of said first slot and said second slot and moved toward said distal end of said member,
wherein said housing further comprises an intermediate slot connecting said first slot and said second slot, and wherein said actuator is configured to slide within said intermediate slot to be selectively positioned within said first slot and said second slot.

19. The surgical stapling instrument of claim 18, wherein said intermediate slot is substantially co-planar with said first slot and said second slot.

20. The surgical stapling instrument of claim 18, wherein said intermediate slot is one of perpendicular to and transverse to said first slot and said second slot.

21. A surgical stapling instrument, comprising:
a housing;
a member configured to operably support a staple cartridge having staples stored therein, wherein at least one of said member and the staple cartridge is configured to slidably support a staple driver configured to deploy the staples from the staple cartridge;
a drive bar configured to move the staple driver relative to said member; and
a first actuator selectively engageable with said drive bar, wherein said first actuator is rotatable between a first position and a second position, wherein said first actuator is operably disengaged from said drive bar when it is in said first position, and wherein said first actuator is operably engaged with said drive bar when it is in said second position; and a second actuator selectively engageable with said drive bar independently of the selective engagement of said first actuator with said drive bar, wherein said second actuator is rotatable between a third position and a fourth position, wherein said second actuator is operably disengaged from said drive bar when it is in said third position, wherein said second actuator is operably engaged with said drive bar when it is in said fourth position, and wherein said first actuator can be rotated between said first position and said second position independently of said second actuator being rotated between said third position and said fourth position.

22. A surgical stapling instrument, comprising:

a housing comprising a first side and a second side;

a first jaw member configured to operably support a staple cartridge comprising at least two rows of staple stored therein, wherein at least one of said first jaw member and the staple cartridge is configured to slidably support a staple driver configured to deploy the staples from the staple cartridge;

a second jaw member configured to operably support an anvil configured to deform the staples when the staples are deployed from the staple cartridge;

a pusher bar configured to move the staple driver relative to said first jaw member and said second jaw member, wherein said pusher bar comprises a first drive portion and a second drive portion;

a guide extending from at least one of said first jaw member and said second jaw member, and an actuator releasably engaged with said guide, wherein said actuator is configured to receive a force thereto, wherein said actuator is selectively disengageable from said guide in a first direction to be engaged with said first drive portion of said pusher bar, wherein said actuator is selectively disengageable from said guide in a second direction to be engaged with said second drive portion of said pusher bar, wherein said actuator is movable along said first side of said housing when said actuator is engaged with said first drive portion of said pusher bar, and wherein said actuator is movable along said second side of said housing when said actuator is engaged with said second drive portion of said pusher bar.

23. The surgical stapling instrument of claim 22, wherein said guide comprises a guide slot, and wherein said actuator is slidably movable through said guide slot between a first position in which it is engaged with said first drive portion of said pusher bar, a second position in which it is engaged with said second drive portion of said pusher bar, and an intermediate position intermediate said first position and said second position in which said actuator is operably disengaged from said pusher bar.

24. A surgical stapling instrument, comprising:

a frame, comprising:
- a first side;
- a second side;
- a first frame member configured to operably support a staple cartridge comprising at least two rows of staple stored therein, wherein at least one of said first frame member and the staple cartridge is configured to slidably support a staple driver configured to deploy the staples from the staple cartridge;
- a second frame member configured to be operably coupled with said first frame member, wherein said second frame member is configured to operably support an anvil configured to deform the staples when the staples are deployed from the staple cartridge;

a pusher bar configured to move the staple driver relative to said first frame member and said second frame member, wherein said pusher bar comprises a first drive portion and a second drive portion;

a guide extending from at least one of said first frame member and said second frame member, and an actuator releasably engageable with said guide, wherein said actuator is configured to receive a force thereto, wherein said actuator is selectively disengageable from said guide in a first direction to be engaged with said first drive portion of said pusher bar, wherein said actuator is selectively disengageable from said guide in a second direction to be engaged with said second drive portion of said pusher bar, wherein said actuator is movable along said first side of said frame when said actuator is engaged with said first drive portion of said pusher bar, and wherein said actuator is movable along said second side of said frame when said actuator is engaged with said second drive portion of said pusher bar.

25. The surgical stapling instrument of claim 24, wherein said guide comprises a guide slot, and wherein said actuator is slidably movable through said guide slot between a first position in which it is engaged with said first drive portion of said pusher bar, a second position in which it is engaged with said second drive portion of said pusher bar, and an intermediate position intermediate said first position and said second position in which said actuator is operably disengaged from said pusher bar.

* * * * *